US006746692B2

(12) United States Patent
Conley et al.

(10) Patent No.: US 6,746,692 B2
(45) Date of Patent: Jun. 8, 2004

(54) MODIFIED RELEASE PHARMACEUTICAL FORMULATION COMPRISING AMOXYCILLIN

(75) Inventors: Creighton P. Conley, Bristol, TN (US); John A. Roush, Kingsport, TN (US); Kevin H. Storm, Bristol, TN (US)

(73) Assignee: Beecham Pharmaceuticals (Pte) Limited, Jurong (SG)

( * ) Notice: Subject to any disclaimer, the term of this patent is extended or adjusted under 35 U.S.C. 154(b) by 0 days.

(21) Appl. No.: 10/115,700

(22) Filed: Apr. 4, 2002

(65) Prior Publication Data

US 2002/0168405 A1 Nov. 14, 2002

Related U.S. Application Data

(62) Division of application No. 09/544,019, filed on Apr. 6, 2000
(60) Provisional application No. 60/129,074, filed on Apr. 13, 1999, provisional application No. 60/150,727, filed on Aug. 25, 1999, and provisional application No. 60/159,813, filed on Oct. 15, 1999.

(51) Int. Cl.[7] .............................. A61K 9/22; A61K 9/20; A61K 9/46; A61K 9/14; A61K 9/00
(52) U.S. Cl. ................ 424/468; 424/464; 424/466; 424/489; 424/482; 424/441; 424/472; 424/470; 424/451; 424/400
(58) Field of Search ................. 424/464, 466, 424/472, 489, 482, 451, 400

(56) References Cited

U.S. PATENT DOCUMENTS

| | | | |
|---|---|---|---|
| 4,282,202 A | 8/1981 | Dowrick | |
| 4,301,149 A | 11/1981 | Crowley | |
| 4,303,582 A | 12/1981 | Shean et al. | |
| 4,427,690 A | 1/1984 | Cole et al. | |
| 4,441,609 A | 4/1984 | Crowley | |

(List continued on next page.)

FOREIGN PATENT DOCUMENTS

| | | |
|---|---|---|
| EP | 0080862 | 11/1982 |
| EP | 0131147 B1 | 1/1985 |
| EP | 0080862 B1 | 9/1985 |
| EP | 0080862 A1 | 9/1985 |
| EP | 0222914 A1 | 5/1987 |
| EP | 0281200 A | 2/1988 |
| EP | 0389177 A | 3/1990 |
| EP | 0396335 A1 | 11/1990 |
| EP | 0131147 B2 | 12/1996 |
| EP | 0131147 B2 * | 12/1996 |
| EP | 1004680 A | 4/2000 |
| GB | 1508977 | 4/1978 |
| GB | 2005538 | 4/1979 |
| HU | 205611 | 4/1991 |
| WO | WO 91/15197 | 10/1991 |
| WO | WO 92/19227 | 11/1992 |

(List continued on next page.)

OTHER PUBLICATIONS

Remington's Pharmaceutical Sciences, Eighteenth Edition, 1990, pp. 1304–1308, 1317–1323.*

Appelbaum, 1996, "Epidemiology and in vitro susceptibility of drug–resistant *Streptococcus pneumoniae*," Ped. Inf. Dis. J., 15(10): 932–939.

Arancibia et al., 1987, "Pharmacokinetics and bioavailability of a controlled release amoxicillin formulation," Int. J. of Clin. Pharm., Ther. and Tox., 25(2): 97–100.

(List continued on next page.)

*Primary Examiner*—Thurman K. Page
*Assistant Examiner*—Rachel M. Bennett
(74) *Attorney, Agent, or Firm*—Dara L. Dinner; Stephen Venetianer; Charles M. Kinzig

(57) ABSTRACT

Bacterial infections may be treated using a high dosage regimen of amoxycillin and potassium clavulanate. Preferably, the dosage is provided by a bilayer tablet.

21 Claims, 7 Drawing Sheets

U.S. PATENT DOCUMENTS

| | | | |
|---|---|---|---|
| 4,525,352 A | 6/1985 | Cole et al. |
| 4,537,887 A | 8/1985 | Rooke et al. |
| 4,673,637 A | 6/1987 | Hyman |
| 4,950,484 A | 8/1990 | Olthoff et al. |
| 5,051,262 A | 9/1991 | Panoz et al. |
| 5,077,790 A | 12/1991 | Shell |
| 5,133,974 A | 7/1992 | Paradissis et al. |
| 5,158,779 A | 10/1992 | Gergely et al. |
| 5,225,197 A | 7/1993 | Bolt et al. |
| 5,407,686 A | 4/1995 | Patel et al. |
| 5,445,829 A | 8/1995 | Paradissis et al. |
| 5,487,901 A | 1/1996 | Conte et al. |
| 5,500,227 A | 3/1996 | Oshlack et al. |
| 5,582,837 A | 12/1996 | Shell |
| 5,650,169 A | 7/1997 | Conte et al. |
| 5,670,170 A | 9/1997 | Grimmett et al. |
| 5,681,583 A | 10/1997 | Conte et al. |
| 5,733,577 A | 3/1998 | Myers et al. |
| 5,738,874 A | 4/1998 | Conte et al. |
| 5,741,524 A | 4/1998 | Staniforth et al. |
| 5,814,337 A | 9/1998 | Merrifield et al. |
| 5,849,330 A | 12/1998 | Marvola et al. |
| 5,858,412 A | 1/1999 | Staniforth et al. |
| 5,962,022 A | 10/1999 | Bolt et al. |
| 5,972,389 A | 10/1999 | Shell et al. |
| 6,027,748 A | 2/2000 | Conte et al. |
| 6,051,254 A | 4/2000 | Merrifield et al. |
| 6,051,255 A | 4/2000 | Conley et al. |
| 6,077,536 A | 6/2000 | Merrifield et al. |
| 6,090,411 A | 7/2000 | Pillay et al. |
| 6,126,969 A | 10/2000 | Shah et al. |
| 6,177,421 B1 | 1/2001 | Moir et al. |
| 6,183,778 B1 | 2/2001 | Conte et al. |
| 6,183,780 B1 | 2/2001 | Van Balken et al. |
| 6,214,359 B1 | 4/2001 | Bax |
| 6,294,199 B1 | 9/2001 | Conley et al. |
| 6,294,200 B1 | 9/2001 | Conte et al. |
| 6,340,475 B2 | 1/2002 | Shell et al. |
| 6,372,255 B1 | 4/2002 | Saslawski et al. |
| 6,399,086 B1 | 6/2002 | Katzhendler et al. |
| 2001/0018070 A1 | 8/2001 | Shell et al. |
| 2001/0026809 A1 | 10/2001 | Oshlack et al. |
| 2001/0038838 A1 | 11/2001 | Burch |
| 2001/0043926 A1 | 11/2001 | Burch |
| 2001/0046984 A1 | 11/2001 | Rudnic |
| 2001/0048944 A1 | 12/2001 | Rudnic et al. |
| 2002/0001616 A1 | 1/2002 | Conley et al. |
| 2002/0004071 A1 | 1/2002 | Cherukuri |
| 2002/0004499 A1 | 1/2002 | Rudnic et al. |
| 2002/0006433 A1 | 1/2002 | Davidson et al. |
| 2002/0099044 A1 | 7/2002 | Bax et al. |

FOREIGN PATENT DOCUMENTS

| | | |
|---|---|---|
| WO | WO 93/00898 | 1/1993 |
| WO | WO 94/06416 | 3/1994 |
| WO | WO 94/16696 | 8/1994 |
| WO | WO 94/27557 | 12/1994 |
| WO | WO 94/27600 | 12/1994 |
| WO | WO 95/20946 * | 8/1995 |
| WO | WO 95/25516 | 9/1995 |
| WO | WO 95/28148 | 10/1995 |
| WO | WO 95/28927 | 11/1995 |
| WO | WO 95/33487 | 12/1995 |
| WO | WO 96/04908 | 2/1996 |
| WO | WO 96/07408 | 3/1996 |
| WO | WO 96/34605 | 11/1996 |
| WO | WO 96/04907 | 12/1996 |
| WO | WO 97/09042 | 3/1997 |
| WO | WO 98/05305 | 2/1998 |
| WO | WO 98/07424 | 2/1998 |
| WO | WO 98/22091 | 5/1998 |
| WO | WO 98/35672 | 8/1998 |
| WO | WO 98/40054 | 9/1998 |
| WO | WO 98/42311 | 10/1998 |
| WO | WO 99/25343 | 5/1999 |
| WO | WO 99/47125 | 9/1999 |
| WO | WO 99/62910 | 12/1999 |
| WO | WO 00/03695 | 1/2000 |
| WO | WO 00/12088 | 3/2000 |
| WO | WO 00/23045 | 4/2000 |
| WO | WO 00/41478 | 7/2000 |
| WO | WO 00/44353 | 8/2000 |
| WO | WO 00/61116 | 10/2000 |
| WO | WO 01/00177 A1 | 1/2001 |
| WO | WO 01/13883 A1 | 3/2001 |
| WO | WO 01/56544 A2 | 8/2001 |
| WO | WO 01/62231 A1 | 8/2001 |
| WO | WO 01/80824 A2 | 11/2001 |
| WO | WO 02/30392 A2 | 4/2002 |
| WO | WO 02/49618 A1 | 6/2002 |
| WO | WO 03/17985 A1 | 3/2003 |

OTHER PUBLICATIONS

Chiou, "Critical Evaluation of the Potential Error in Pharmacokinetic Studies of Using the Linear Trapezoidal Rule Methd for the Calculation of the Area Under the Plasma Level–Time Curve," 1978, J. Pharmicokinet. Biopharm., 6(6): 539–546.

Hilton et al., 1992, "In vitro and in vivo evaluation of an oral sustained–release floating dosage form of amoxycillin trihydrate," Int. J. of Pharmaceutics, 86: 79–88.

Hilton et al., 1993, "Use of Hydroxypropyl Methylcellulose Acetate Succinate in an Enteric Polymer Matrix to Design Controlled–Release Tablets of Amoxicillin Trihydrate," J. Pharmaceutical Sciences, 82(7): 737–743.

Hoffman, et al., 1998, "Pharmacodynamic and Pharmacokinetic rationales for the development of an oral controlled–release amoxicillin dosage form," J. Controlled Release, 54: 29–37.

Physicians' Desk Reference, 1998, 52$^{nd}$ Edition, Medical Economics Co., Montvale, NJ, p. 2798–2805.

Caillon et al., May 1998, "Dynamics of the bacteriacidae activity of ofloxacin–amoxicillin and ofloxacin–clavulanic acid against pathogen bacteria of the respiratory tract", Pathologie Biologie, 36(5), pp. 414–419.

Greenwood, D., "Short Communication: a type of interaction between calvulanic acid and other β–lactam antibiotics distinct from the β–lactamase inhibition effect," from Augmentin: clavulanate–potentiated amoxycillin, Proceeding of the First Symposium, July 3–4, 1980, pp. 80–83.

Physicians' Desk Reference, 40$^{th}$ Edition, 1986, "Amoxycillin," pp. 1315–1316.

Segatore, et al., 1993, "In vitro Activity of Cefodizime (HR–221) in Combination with β–Lactamase Inhibitors," Journal of Chemotherapy, vol. 5, No. 3, pp. 147–150.

Sumita et al., 1991, "In vitro Synergistic Activity between Meropenem and other Beta–Lactams against Methicillin–Resistant *Staphylococcus aureus*," European Journal of Clinical Microbiology and Infectious Diseases, vol. 10, No. 2, pp. 77–84.

Brooks et al., "Pleuromutilins, Part 1: The Identification of Novel Mutilin 14–Carbamates,"0 Bioorganic and Medicinal Chemistry 9, 2001, pp. 1221–1231.

Catherall et al., "Distribution and Efficacy Studies with Ticarcillin–Clavulanic Acid (Timentin) in Experimental *Klebsiella Pneumoniae* Meningitis in Rabbits", Journal of Chemotherapy, 1989 supplement No. 4, pp. 80–81.

Everett et al., "$^{19}$F NMR Spectroscop0y Study of the Metabolites of Flucloxacillin in Rat Urine," Journal of Pharm. Pharmacology, 1985, vol. 37, pp. 869–873.

Everett et al., "A Study of Flucloxacillin Metabolites in Rat Urine by Two–Dimensional $^1$H, $^{19}$F COSY NMR," Journal of Pharmaceutical & Biomedical Analysis, 1989, vol. 7, No. 3, pp. 397–403.

Everett et al., "Spin–echo $^1$H N.M.R. spectroscopy: A new method for studying penicillin metabolism," J. Chem. Soc. Chem. Commun., 1984, pp. 894–895.

Hannan et al., "In Vitro Activity of Gemifloxacin (SB 265805; LB 20304a) against human mycoplasmas," Journal of Antimicrobial Chemotherapy, 2000, vol. 45, pp. 367–369.

Ji et al., "Identification of Critical Staphylococcal Genes Using Conditional Phenotypes Generated by Antisense RNA", Science Reprint, Sep. 21, 2001, vol. 293, pp. 2266–2269.

Ji et al.,"Regulated Antisense RNA Eliminates Alpha–Toxin Virulence in *Staphylococcus aureus* Infection", Journal of Bacteriology, Nov. 1999, pp. 6585–6590.

Mizen et al., "Simulation of Human Serum Pharmacokinetics of Ticarcillin–Clavulanic Acid and Ceftazidime in Rabbits and Efficacy Against Experimental *Klebsiella Pneumoniae* Meningitis", Antimicrobial Agents and Chemotherapy, May 1989, vol. 33, No. 5, pp. 693–699.

Woodnutt et al., "Acetate entry rate into portal and peripheral blood in the rabbit", Proc. Nutr. Soc., 1979, vol. 38, p.72A.

Woodnutt et al., "Acetate Metabolism By Tissues of the Rabbit", Comp. Biochemical Physiol, 1986, vol. 85B, No. 2, pp. 487–490.

Woodnutt et al., "Pharmacokinetics and Distribution of Ticarcillin–Clavulanic Acid (Timentin) in Experimental Animals", Antimicrobial Agents and Chemotherapy, 1987, vol. 31, No. 11, pp. 1826–1830.

Woodnutt et al., "Rabbit liver acetyl–CoA synthetase", Biochem J., 1978, vol. 175, pp. 757–759.

Woodnutt et al., "Simulation of Human Serum Pharmacokinetics of Cefazolin, Piperacillin, and BRL 42715 in Rats and Efficacy Against Experimental Intraperitoneal Infections", Antimicrobial Agents and Chemotherapy, Jul. 1992, vol. 36, No. 7, pp. 1427–1431.

Woodnutt et al., "Temocillin Efficacy in Experimental *Klebsiella Pneumoniae* Meningitis after infusion into Rabbit Plasma To Simulate Antibiotic Concentrations in Human Serum", Antimicrobial Agents and Chemotherapy, Nov. 1988, vol. 32, No. 11, pp. 1705–1709.

Flatulence, Diarrhoea, and Polyol Sweetners, The Lancet, Dec. 3, 1983, vol. II, p. 1321.

Murbach et al., "Mise en évidence in vitro d'un véritable effet post–inhibiteur de bêta–lactamases (EPIBLA) de l'acide clavulanique sur *Klebsiella pneumoniae* et *Haemophilus influenzae,*" Path Biol, 1999, 47(5): 462–468.

Amendola, et al., "Pediatric suspension of amoxycillin and clavulanic acid in the treatment of bacterial infections of the upper respiratory tract and ear", Minerva Pediatrica, 1989, vol. 41, No. 2, pp. 97–103.

Arguedas et al., "In–vitro activity of cefprozil (BMY 28100) and loracarbef (LY 163892) against pathogens obtained from middle ear fluid", J. Antimicrob. Chemother., 1991, 27(3), pp. 311–318.

Astruc, "Efficacy and tolerance of a new formulation amoxicillin 100 mg—clavulanic acid 12.5 mg in acute otitis media in infants", Annales De Pediatrie, 1992, vol. 39, No. 2, 142–148.

Aulton et al., "The Mechanical Properties of Hydroxypropylmethylcellulose Films Derived from Aqueous Systems", Drug Development and Industrial Pharmacy, 1981, 7(6), pp. 649–668.

Ball et al., "Clavulanic Acid and Amoxycillin: A Clinical, Bacteriological, and Pharmacological Study", The Lancet, Mar. 22, 1980, vol. 1, pp. 620–623.

Baron et al., "Antimicrobial therapy in acute otitis media", Traitement Antibiotique de L'Otite Moyenne Aigue, Annales de Pediatrie, 1991, 38(8), pp. 549–555.

Barry et al., "Effect of Increased Dosages of Amoxycillin in Treatment of Experimental Middle Ear Otitis Due to Penicillin–Resistant *Streptococcus pneumoniae*", Antibacterial Agents and Chemotherapy, Aug. 1993, vol. 37, No. 8, pp. 1599–1603.

Beghi et al., "Efficacy and Tolerability of Azithromycin versus Amoxicillin/Clavulanic Acid in Acute Purulent Exacerbation of Chronic Bronchitis", Journal of Chemotherapy, 1995, 7(2), pp. 146–152.

Berry et al., "Comparative Efficacy of Gemifloxacin in Experimental Models of Pyelonephritis and Wound Infection", Journal of Antimicrobial Chemotherapy, 2000, No. 45, supplement S1 pp. 79–85.

Bottenfield et al., Safety and Tolerability of a New Formulation . . . In the Empiric Treatment of Pediatric . . . *Streptococcus pneumoniae,* Pediatrict Infect. Dis. J., vol. 17, pp. 963–968 (1998).

Calver et al., "Amoxicillin/Clavulanate BID vs A/C TID in the Treatment of Lower Respiratory Tract Infections", Abstracts of the 35th ICAAC, 1995, p. 334.

Calver et al., "Augmentin Bid Versus Augmentin TID in the Treatment of Lower Respiratory Tract Infections", Can. J. Infect Dis., 1995, vol. 6 Suppl C, Abstract No. 0338, p. 239C ABSTRACT.

Calver et al., "Dosing of Amoxicillin/Clavulanate Given Every 12 Hours is as Effective as Dosing Every 8 Hours for Treatment of Lower Respiratory Tract Infection", Clinical Infectious Disease, 1997, 24, pp. 570–574.

Caron et al., "Effects of Amoxicillin–Clavulanate Combination on the Motility of the Small Intestine in Human Beings", Antimicrobial Agents and Chemotherapy, Jun. 1991, vol. 35 No. 6, pp. 1085–1088.

Cars, "Efficacy of Beta–lactam Antibiotics", Diagn Microbiol Infect Dis, 1997, 27 pp. 29–33.

Chan et al., "A comparative study of amoxicillin–clavulanate and amoxicillin. Treatment of otitis media with effusion." Archives of Otolaryngology—Head and Neck Surgery, Feb. 1988, 114(2), pp. 142–146.

Connor et al., "High Resolution 1H NMR spectroscopic Studies of the Metabolism and Excretion of amplicillin in Rats and Amoxycillin in Rats and Man", Journal of Pharm. Pharmacol. 1994, vol. 46 pp. 128–134.

Cook et al., "Efficacy of Twice–Daily Amoxycillin/Clavulanate etc.", BJC, 50(3), 1996, pp. 125–128.

Cooper et al., "Effect of low concentrations of clavulanic acid on the in–vitro activity of amoxycillin against B–lactamase–producing *Branhamella catarrhalis* and *Haemophilus influenzae*", Journal of Antimicrobial Chemotherapy, 1990, vol. 26, pp. 371–380.

Craig, "Antimicrobial Resistant Issues of the Future", Diagn Microbiol Infect Dis, 1996, 25, pp. 213–217.

Craig et al., "Killing and Regrowth of Bacteria in Vitro: A Review", Scand J Infect Dis., 1991, Suppl 74, pp. 63–70.

Craig et al., "Pharmacokinetics and pharmacodynamics of antibiotics in otitis media", Pediatr Infect Dis J, 1996, 15, pp. 255–259.

Craig, "Pharmacokinetic/Pharmacodynamic Parameters: Rationale for Antibacterial Dosing of Mice and Men", Clinical Infectious Diseases, 1998, 26, pp. 1–12.

Crokaert et al., "Activities of Amoxicillin and Clavulanic Acid Combinations Against Urinary Tract Infections", Antimicrobial Agents and Chemotherapy, Aug. 1982, vol. 22 No. 2, pp. 346–349.

Dagan et al., "Bacteriologic and clinical efficacy of high dose amoxicillin/clavulanate in children with acute otitis media", Pediatric Infectious Diseases Journal, 2001, vol. 20, pp. 828–837.

Ellis–Pegler et al., "Augmentin treatment of bacterial infections in hospitalized patients", New Zealand Medical Journal, 1982, 95(713), pp. 542–545.

Feldman et al., "Twice–daily antibiotics in the treatment of acute otitis media: trimethoprimsulfamethoxazole versus amoxicillin–clavulanate", Can Med. Assoc. J., 1990, 142(2), pp. 115–118.

Finch, "Pneumonia: The Impact of Antibiotic Resistance on its Management", Microbial Drug Resistance, vol. 1, No. 2, 1995, pp. 149–158.

Fink et al., "A trial of orally administered Augmentin in the treatment of urinary tract infection and lower respiratory tract infection in a children's hospital", Proc Eur Symp on Augmentin, Scheveningen Jun. 1982, 1983: pp. 325–333.

Fraschini et al., "Pharmacokinetics and Tissue Distribution of Amoxicillin plus Clavulanic Acid after Oral Administration in Man", Journal of Chemotherapy, 1990, 2(3), pp. 171–177.

Friedland et al., "Management of Infections caused by Antibiotic–Resistant *Streptococcus Pneumoniae*", The New England Journal of Medicine, 1994, vol. 331, No. 6, pp. 377–382.

Heikkinen et al., "Short–term use of amoxicillin–clavulanate during upper respiratory tract infection for prevention of acute otitis media", The Journal of Peds, Feb. 1995, 126(2), pp. 313–316.

Hoberman et al., "Efficacy of amoxicillin/clavulanate for acute otitis media: relation to *Streptococcus pneumoniae* susceptibility", Pediatr Infect Dis Jr., 1996(15), pp. 955–962.

Hoberman et al., "Equivalent efficacy and reduced occurrence of diarrhea from a new formulation etc.", Journal of Pediatric Infect. Dis., 1997, 16, pp. 463–470.

Hol et al., "Experimental evidence for Moraxella–induced penicillin neutralization in *pneumococcal pneumonia*", Journal of Infectious Diseases, 1994, 170(6), pp. 1613–1614.

Jacobsen et al., "Evaluation of Amoxicillin Clavulanate Twice Daily versus Thrice Daily in the Treatment of Otitis Media in Children", Eur. J. Clin. Microbiol. Infect. Dis., May 1993, pp. 319–324.

Jeffries et al., "An Initial Assessment of Augmentin for the Treatment of Paediatric Infections in General Practice", The British Journal of Clinical Practice, 1996, pp. 61–66.

Klein, "Antimicrobial Agents", Therapeutics—Part V, 1992, pp. 2179–2198.

Kucer et al., "Ampicillin–like penicillins—Amoxycillin, Epicillin, Cyclacillin, Hetacillin, Pivampicillin, Talampicillin, Bacampicillin and Metampicillin", 2) "Clavulanic Acid", The Use of Antibiotics, 1987, pp. 172–195/271–286.

Lachman et al., "Tablet Granulations", The Theory and Practice of Industrial Pharmacy, 1986, pp. 314–320.

Legent et al., Chemotherapy (Based), "A Double–Blind Comparison of Ciprofloxacin and Amoxycillin/Clavulanic Acid in the Treatment of Chronic Sinusitis", 40(Suppl. 1), 8–15, (1994).

Lerk et al., "Interaction of lubricants and colloidal silica during mixing with excipients", Pharmacuetica Acta Helvetiae, 1997, 52(3) pp. 33–39.

Lieberman et al., "Pharmaceutical Dosage Forms—Tablets Second Edition, Revised and Expanded", 1989, vol. 2, pp. 317–334.

Lister et al., "Rationale behind High–Dose Amoxicillin Theraphy for Acute Otitis Media Due to Penicillin–Nonsusceptible Pnsumococci: Support from In Vitro Pharmacodynamic Studies", Antimicrobial Agents and Chemotherapy, Sep. 1997, vol. 41, No. 9, pp. 1926–1932.

McCracken, "Emergence of resistant *Streptococcus pneumoniae*: a problem in pediatrics", Pediatr Infect Dis J, 1995, 14, pp. 424–428.

McLaren et al., "A comparison of the efficacy and tolerability of Augmentin 625 mg po bd versus Augmentin 375 mg po tds in the tratment of acute bacterial exacerbations of chronic bronchitis", British Journal Clin Research, 1994 (5) pp. 1–10.

Mizen et al., "A Critique of Animal Pharmacokinetics", Journal of Antimicrobial Chemotherapy, 1988, vol. 21, pp. 273–280.

Mizen et al., "The Influence of Uptake from the Gastrointestinal Tract and First–pass Effect on Oral Bioavailability of (Z)–alkyloxyimino Penicillins", Journal of Pharm. Pharmacology, 1995, vol. 47, pp. 725–730.

Moonsammy et al., "Improved Safety Profile of a New Amoxicillin/Clavulanate Adult BID Formulation Compared with the Standard A/C TID Formulation", Abstracts of the 36th ICAAC, 1996, p. 290.

Neu, "Other B–Lactam Antibiotics", Principles and Practice of Infectious Diseases, 1990, pp. 257–263.

Neville, "Augmentin: An in vitro study of bacterial sensitivities to a synergistic combination", New Zealand Medical Journal, 1982, 95(714), pp. 579–581.

Nicolau et al. "Antibiotic Kinetics and Dynamics for the Clinician", Antimicrobial Therapy I, vol. 79 No. 3, May 1995.

Okhamapet et al., "Characterization of moisture interactions in some aqueous–based tablet film coating formulations", Journal Pharm Pharmacol, 1985(37), pp. 385–390.

Pankuch et al., "Comparative activity of ampicillin, amoxycillin, amoxycillin/clavulanate and cefotaxime against 189 penicillin susceptible and –resistant pneumococci", Journal of Antimicrobial Chemotherapy, 1995, 35, 883–888.

Parrott, "Densification of Powders by Concavo–Convex Roller Compactor", Journal of Pharm Sciences, Mar. 1981, vol. 70(3), pp. 288–291.

Pichichero, "Resistant respiratory pathogens and extended–spectrum antibiotics", American Family Physican, 1995, 52(6), pp. 1739–1746.

Robinson, "Amoxicillin trihydrate/Clavulanic acid potassium salt", Med. Actual., 1982, 18(5) pp. 213–219.

Ruberto et al., "Amoxycillin and Clavulanic Acid in the Treatment of Urinary Tract Infections in Children", Journal of International Medical Research, 1989, 17, pp. 168–171.

Saarnivaara et al., "Effect of Storage on the Properties of Acetylsalicylc Acid Tablets Coated with Aqueous Hydroxypropyl Methyl–Cellulose Dispersion", Drug Develop and Ind Pharmacy, 1985, 11(2&3), pp. 481–492.

Sakellariou et al., "An evaluation of the interaction and plasticizing efficiency of the polyethylene glycols in theyl cellulose and hydroxypropyl methylcellulose films using the torsional braid pendulum", Int Journal of Pharm, 1986(31), pp. 55–64.

Staniforth et al., "Effect of food on the bioavailability and tolerance of clavulanic acid/amoxycillin combination", Journal of Antimicrobial Chemotherapy, (1982) 10, pp. 131–139.

Stein et al., "Amoxicillin–potassium clavulanate, a B–lactamase–resistant antibiotic combination", Clinical Pharmacy, vol. 3, Nov.–Dec. 1984 pp. 591–599.

Todd et al., "Amoxicillin/Clavulanic Acid—An Update of its Antibacterial Activity, Pharmcokinetic Properties and Therapeutic Use", Drugs, 1990, 39(2), pp. 264–307.

Toh, "Amoxycillin with clavulanic acid", The Autstralian Nurses Journal, Dec./Jan. 1995, vol. 18, No. 6, Abstract.

Tondachi et al., "Tablet Coating in an Aqueous System", Drug Develop and Ind Pharmacy, 1977, 3(3), pp. 227–240.

Van Niekerk, "Pharmacokinetic Study of a Paediatric Formulation of Amoxycillin and Clavulanic Acid in Children", European Journal of Clinical Pharmacoloy, 1985, 29, pp. 235–239.

Woodnutt et al., Antimicrobial Agents and Chemotherapy, "Efficacy of High–Dose Amoxicillin–Clavulanate against Experimental Respiratory Tract Infections Caused by Strains of *Streptococcus pneumonia*", 43(1), 35–40, (1999).

Woodnutt et al., "Effect of Protein Binding on Penetration of B–Lactams into Rabbit Peripheral Lymph", Antimicrobial Agents and Chemotherapy, Dec. 1995, vol. 39, No. 12, pp. 2678–2683.

Woodnutt et al., "Efficite de l'association amoxicilline–acide clavulanique dans un modele d'abces sous–cutane a *E. coli* chez rat apres simulation de l'administration chez l'homme de lg/200mg (IVD) ou de 2g/200mg (perfusion). La lettre de l'infectiologie de la microbiologie a la clinique". Numero hors–serie. 1995, pp. 23–26.

Woodnutt et al., "Influence of Simulated Human Pharmacokinetics on the Efficacy of Temocillin Against a *Klebsiella Pneumoniae* Meningitis Infection in the Rabbit", Journal of Chemotherapy, 1989, supplement No. 4, pp. 475–476.

Woodnutt et al., "Penetration of Amoxycillin, Ticarcillin and Clavulanic Acid into Lymph After Intravenous Infusion in Rabbits to Simulate Human Serum Pharmacokinetics", Journal of Antimicrobial Chemotherapy, 1990, vol. 26, pp. 695–704.

Woodnutt et al., "Penetration of augmentin and timentin into lymph after simulation of human serum pharmacokinetics in the rabbit", Journal of Chemotherapy, 1989, Supplement 4, pp. 477–478.

Woodnutt et al., "Pharmacodynamics to Combat Resistance", Journal of Antimicrobial Chemotherapy, 2000, vol. 46, *Topic T1*, pp. 25–31.

Woodnutt et al., "The Use of Two Pharmacodynamic Models for Assessing the Efficacy of Amoxicillin–Clavulanate against Experimental Respiratory Tract Infections Caused by Strains of *Streptococcus pneumoniae*", Antimicrobial Agents and Chemotherapy, Jan. 1999, vol. 43, No. 1, pp. 29–34.

Woodnutt et al., "Evaluation of reduced dosing schedule of amoxicillin (AMX) using two pharmacodynamic models", Abstracts of the 36th ICAAC, A40, 1995.

1996 MIMS Annual, Twentieth Edition, May 1995, pp. 8–476 to 8–477.

Martindale, The Extra Pharmacopoeia, Thirtieth Edition, Edited by James E. F. Reynolds (London, The Pharmaceutical Press, 1993), pp. 115–116 and 148.

Merck Index 1989, 610 and 2342.

Repertorio Farmaceutico Italiano, 3rd Edition 1989, A106 to A108.

Therapeutic Drugs, Dollery, 1999, pp. C253–C256.

Vidal 1994, 70th Edition, pp. 132–134 (Translation Included).

Bronner S. et al., "Ex vivo pharmacodynamics of 1.1 g IV amoxicillin–clavulanic acid against B–lactamases . . . ", Antibiotiques, 2001, 3/2, pp. 91–98.

Dagan et al., "Bacteriologic and clinical efficacy of high dose amoxicillin/clavulanate in children with acute otitis media", Pediatric Infectious Diseases Journal, 2001, vol. 20, pp. 829–837.

* cited by examiner

PROCESS FLOW DIAGRAM FOR THE MANUFACTURE OF THE IMMEDIATE RELEASE LAYER.
(BATCH SIZE 900Kg)

PROCESS FLOW DIAGRAM FOR THE MANUFACTURE
OF THE SLOW RELEASE LAYER.
(BATCH SIZE 700Kg.)

PROCESS FLOW DIAGRAM FOR TABLETTING
AND COATING OF TABLETS
(300Kg PER SUB-BATCH)

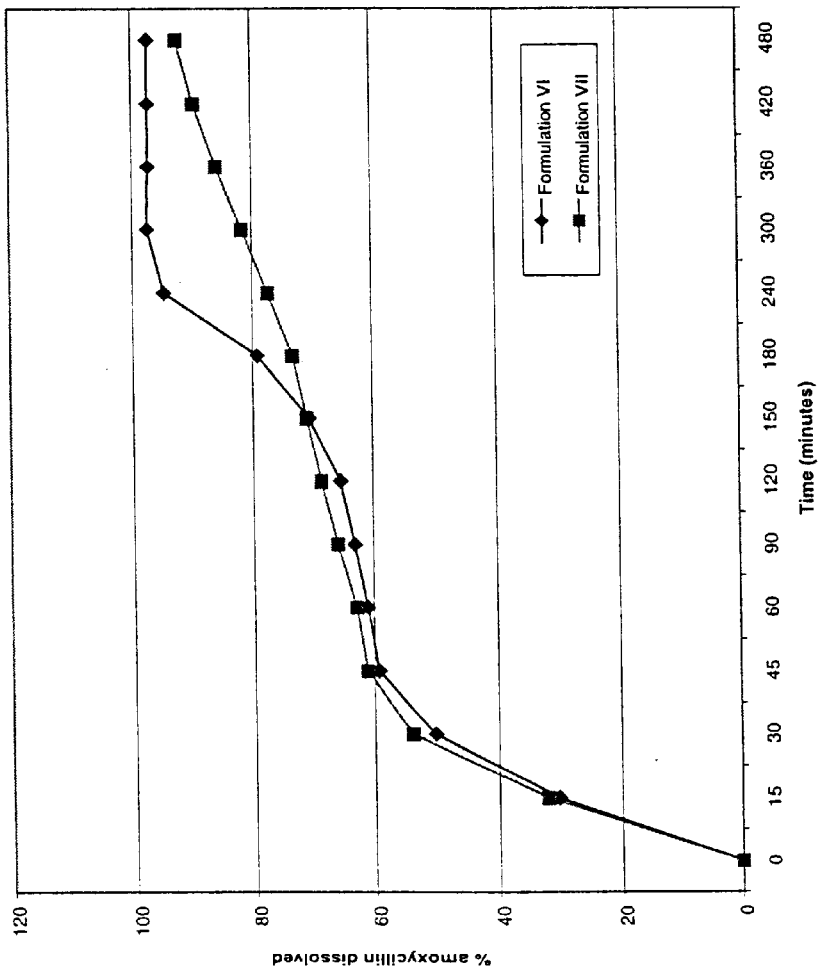
Figure 3 – Dissolution Profile for tablets of Examples 1 and 2

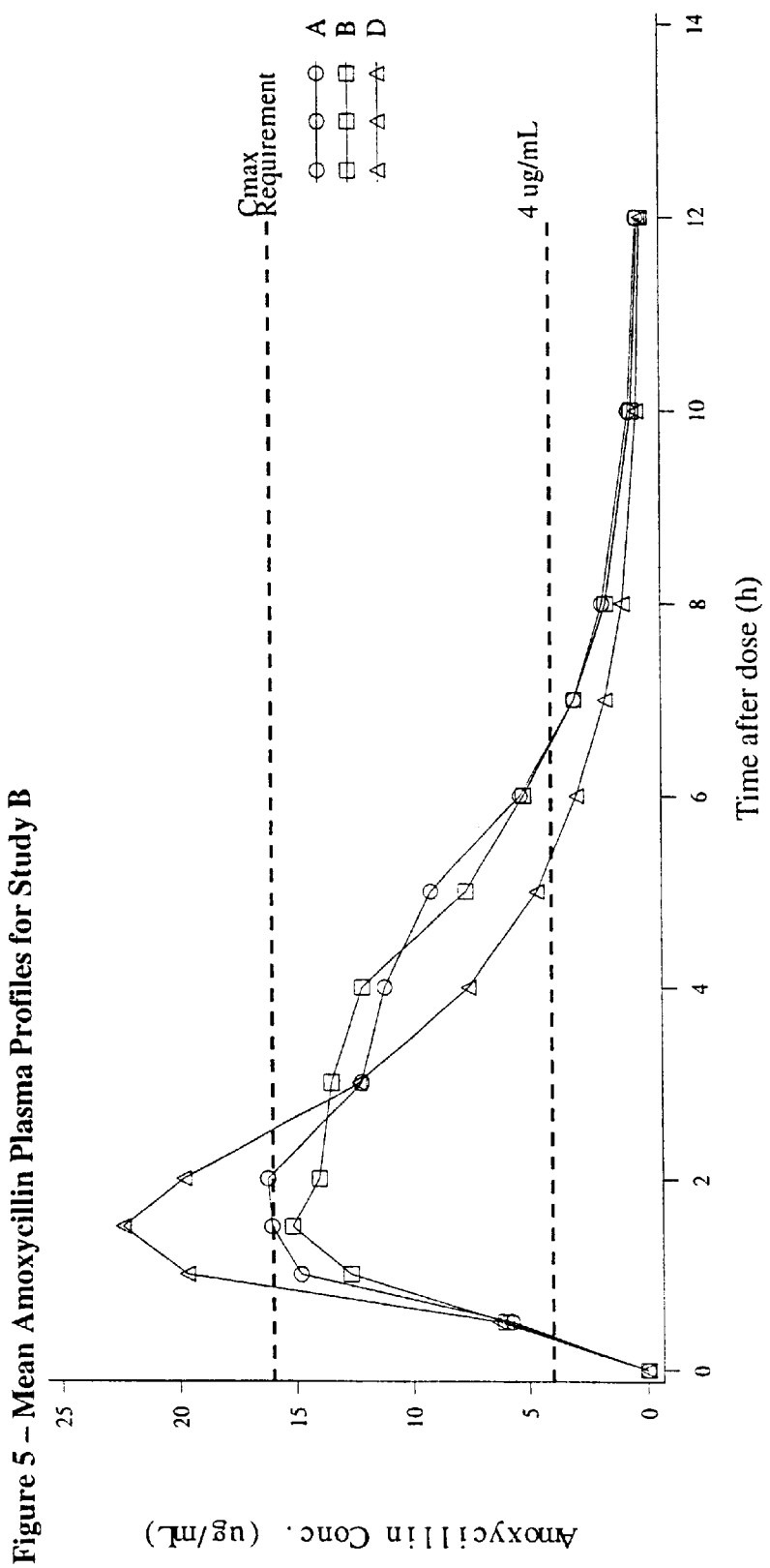
Figure 5 – Mean Amoxycillin Plasma Profiles for Study B

US 6,746,692 B2

MODIFIED RELEASE PHARMACEUTICAL FORMULATION COMPRISING AMOXYCILLIN

This is a divisional of application Ser. No. 09/544,019 filed Apr. 6, 2000 which claims the benefit of priority from the following applications: No. 60/129,074 filed Apr. 13, 1999, No. 60/150,727 filed Aug. 25, 1999 and No. 60/159,813 filed Oct. 15, 1999.

FIELD OF THE INVENTION

This invention relates to a novel method of treatment using amoxycillin and potassium clavulanate and for novel formulations, in particular tablet formulations, for use in such methods.

BACKGROUND OF THE INVENTION

Amoxicillin and potassium clavulanate are respectively a known β-lactam antibiotic and a known β-lactamase inhibitor. Products comprising amoxycillin and potassium clavulanate are marketed under the trade name "Augmentin" by SmithKline Beecham. Such products are particularly effective for treatment of community acquired infections, in particular upper respiratory tract infections in adults and otitis media in children.

Various tablet formulations of amoxycillin and potassium clavulanate have been approved for marketing, comprising various different weights and ratios of amoxycillin and potassium clavulanate, for instance, conventional swallow tablets comprising 250/125, 500/125, 500/62.5, and 875/125 mg amoxycillin/clavulanic acid (in the form of potassium clavulanate). Such tablets comprise amoxycillin and clavulanic acid in the ratio 2:1, 4:1, 8:1 and 7:1, respectively. The 875/125 mg tablet was developed to provide a tablet formulation which could be administered in a bid (twice daily) dosage regimen It is also marketed for tid (three times daily) dosing, in Italy and Spain. The 500/62.5 mg tablet was also developed to provide a tablet formulation which could be administered in a bid dosage regimen, two such tablets being taken every 12 h, in preference to a single 1000/125 mg tablet. A 1000/125 mg single dosage is also available, in France, but as a single dosage sachet rather than a tablet. Typically, the approved regimens provides a single dosage of 125 mg of potassium clavulanate.

In addition, WO 97/09042 (SmithKline Beecham) describes tablet formulations comprising amoxycillin and clavulanic acid in a ratio in the range 12:1 to 20:1, preferably 14:1. Furthermore, it is suggested that the preferred dosage of 1750/125 mg may be provided as two tablets, the first comprising 875/125 mg amoxycillin and clavulanic acid and the second 875 mg amoxycillin. The 14:1 ratio is said to be useful for the empiric treatment of bacterial infection potentially caused by drug resistant *S pneumoniae* (DRSP). This patent application also describes paediatric formulations comprising amoxycillin and clavulanate in a 14:1 ratio, for administering amoxycillin dosages of 90 mg/kg/day. Data suggest that such a dosage may provide antibiotic concentrations sufficient to eradicate DRSP with amoxycillin +/- clavulanic acid MICs≦4 μg/ml (Bottenfield et al, Pediatr Infect Dis J, 1998, 17, 963–8).

WO 94/16696 (SmithKline Beecham) discloses generally that clavulanic acid may unexpectedly enhance the efficacy of amoxycillin against microorganisms having a resistant mechanism which is not β-lactamase mediated.

Existing marketed tablet formulations of amoxycillin and potassium clavulanate are conventional in that they provide immediate release of the active ingredients once the tablet reaches the stomach. There has also been some interest in developing formulations in which the release profile is modified, to allow for a longer interval between dosages, for instances, every 12 hours (bid, q12 h), rather than every 8 hours (tid, q8 h).

Thus, for instance, WO 95/20946 (SmithKline Beecham) describes layered tablets comprising amoxycillin and, optionally, potassium clavulanate, having a first layer which is an immediate release layer and a second layer which is a slow release layer. The broadest ratio of amoxycillin to clavulanic acid is 30:1 to 1:1, with a preferred range of 8:1 to 1:1. Amoxycillin is suitably in the form of amoxycillin trihydrate. Examples provided of such bilayered tablets have amoxycillin trihydrate in the immediate release layer and amoxycillin plus clavulanate in the slow release layer. Multi-layered tablets are described more generically in WO 94/06416 (Jagotec AG). Further bilayered tablets comprising clavulanic acid and amoxycillin are described in WO 98105305 (Quadrant Holdings Ltd). In such tablets, a first layer comprises amoxycillin and a second layer comprises clavulanate and the excipient trehalose, to stabilise the clavulanate component.

In addition, WO 95/28148 (SmithKline Beecham) describes amoxycillin/potassium clavulanate tablet formulations having a core containing amoxycillin and potassium clavulanate coated with a release retarding agent and surrounded by an outer casing layer of amoxycillin and potassium clavulanate. The release retarding agent is an enteric coating, so that there is an immediate release of the contents of the outer core, followed by a second phase from the core which is delayed until the core reaches the intestine. Furthermore, WO 96/04908 (SmithKline Beecham) describes amoxycillin/potassium clavulanate tablet formulations which comprise amoxycillin and potassium clavulanate in a matrix, for immediate release, and granules in a delayed release form comprising amoxycillin and potassium clavulanate. Such granules are coated with an enteric coating, so release is delayed until the granules reach the intestine. WO 96/04908 (SmithKline Beecham) describes amoxycillin/potassium clavulanate delayed or sustained release formulations formed from granules which have a core comprising amoxycillin and potassium clavulanate, surrounded by a layer comprising amoxycillin. WO 94/27557 (SmithKline Beecham) describes controlled release formulations of amoxycillin and clavulanic acid prepared using a hydrophobic waxy material which is then subjected to thermal infusion.

Controlled release formulations comprising amoxycillin have been described by several groups. Thus, Arancibia et al ((Int J of Clin Pharm, Ther and Tox, 1987, 25, 97–100) describe the pharmacokinetic properties and bioavailability of a controlled release formulation comprising 500 mg of amoxycillin. No further details of the formulation are provided. The formulation was however designed to release 21 to 35% during the first 60 minutes, 51 to 66% at 4 hours, 70 to 80% at 6 hours, 81 to 90% at 8 hours and more than 94% at 12 hours. They however found little, if any, correlation between the in vitro dissolution rate and the pharmacokinetic behaviour in the body. Hilton et al (International Journal of Pharmaceutics, 1992, 86, 79–88) described an alternative controlled release tablet having a hydrophilic polymer matrix and a gas release system, to provide intragastric buoyancy, to enhance gastric retention time. This showed no advantage over a conventional capsule formulation, with bioavailability being diminished. In contrast, Hilton et al (Journal of Pharmaceutical Sciences, 1993, 82, 737–743) described a 750 mg controlled release tablet incorporating the enteric polymer hydroxypropylmethyl cellulose acetate succinate. This however failed to show any advantage over a conventional capsule. In particular, the bioavailability was reduced to 64.6% compared with the same dosage provided in a capsule. More recently, Hoffman et al (Journal of Controlled Release, 1998, 54, 29–37 and WO 98/22091) have described a tablet comprising 500 mg of amoxycillin in a matrix comprising hydroxypropyl methyl cellulose, designed to release 50% of its contents in the first three hours and complete the drug release process over eight hours. The time above MIC was found to be significantly extended, compared to a capsule formulation, but not enough for a 12 h dosing interval. The discussion is in the context of a theoretical MIC of 0.2 µg/ml.

It has therefore, been determined that there is a continuing need to provide new dosage regimens for amoxycillin/clavulanate which are effective against more resistant bacteria.

SUMMARY OF THE INVENTION

The present invention relates to a method of treating bacterial infections in humans which comprises administering thereto a therapeutically effective amount of amoxycillin and potassium clavulanate such that the amount of amoxycillin is in the range 1900 to 2600 mg and the amount of potassium clavulanate is such that the weight ratio of amoxycillin to clavulanate is from about 2:1 to 20:1, an at a dosage regiment/interval of about 12 hours. Suitably, the infection is caused by the organisms *S pneumoniae* (including Drug Resistant and Penicillin Resistant *S pneumoniae*), *H influenzae* and/or *M catarrhalis*.

The present invention also relates to a modified release pharmaceutical formulation comprising amoxycillin and potassium clavulanate in the ratio from 2:1 to 20:1 in which all of the potassium clavulanate and a first part of amoxycillin are formulated with pharmaceutically acceptable excipients which allow for immediate release of the potassium clavulanate and the first part of amoxycillin, to form an immediate release phase, and further comprising a second part of amoxycillin formulated with pharmaceutically acceptable excipients which allow for slow release of the second part of amoxycillin, to form a slow release phase.

The present invention also relates to an immediate release pharmaceutical tablet formulation comprising 1000 mg±5% amoxycillin and 62.5 mg±5% potassium clavulanate, in a nominal ratio of about 16:1, in combination with pharmaceutically acceptable excipients or carriers.

The present invention also relates to an immediate release pharmaceutical formulation in the form of a single dose sachet comprising 2000, 2250 or 2500 mg±5% amoxycillin and 125 mg±5% potassium clavulanate, in a nominal ratio of about 16:1, 18:1 or 20:1, respectively, or the corresponding half quantities thereof, in combination with pharmaceutically acceptable excipients or carriers.

Other suitable modified or immediate release formulations are described herein in greater detail.

BRIEF DESCRIPTION OF THE DRAWINGS

FIG. 1 shows the structure of various types of layered tablets of the present invention, in particular the structure of substantially cylindrical compressed tablets are shown in longitudinal section.

FIG. 3 demonstrates the dissolution profile for tablets of Examples 1 and 2.

FIG. 5 demonstrates the pharmacokinetic profile for amoxycillin plasma concentration for Study B (in which A is formulation V, B is formulation VI, D is formulation VIII).

DETAILED DESCRIPTION OF THE INVENTION

Figure 1A:
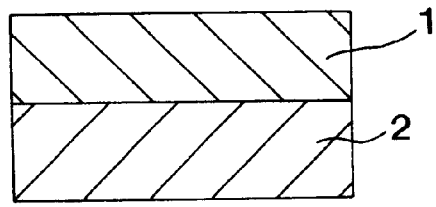
In FIG. 1A, shows a tablet comprising a first layer (1) and a second layer (2), without any barrier layer or coating layer.
Figure 1B:
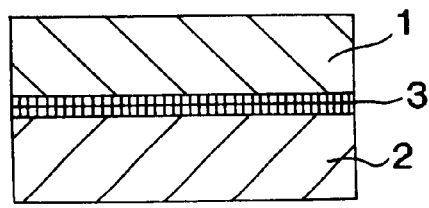
FIG. 1B, shows a tablet comprising a first layer (1), a second layer (2), and a barrier layer (3) sandwiched between the first and second layers (1) and (2).
Figure 1C:
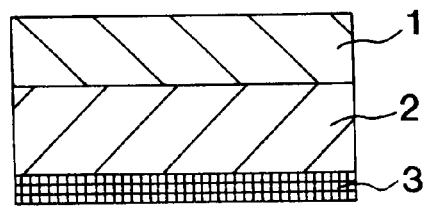
FIG. 1C, shows a tablet comprising a first layer (1), a second layer (2), and a barrier layer (3) located on the end face of the second layer (2).
Figure 1D:
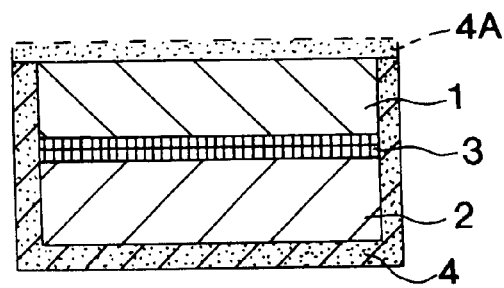
FIG. 1D, shows a tablet comprising a first layer (1), a second layer (2), a barrier layer (3) sandwiched between the first and second layers (1) and (2), and a coating layer (4) which partly covers the tablet. The dotted line shows the possibility of the coating layer (4A) covering the entire tablet.
Figure 1E:
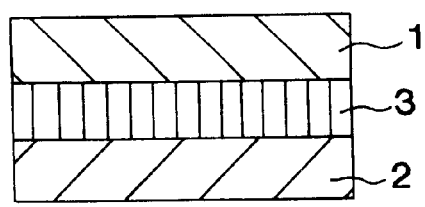
FIG. 1E, shows a tablet comprising a first layer (1) a second layer (2), and a third layer (3) intermediate between the first and second layers (1) and (2). All three of these layers (1), (2) and (3) include active material content.

Part of the challenge in providing formulations of amoxycillin in which the drug release is effectively modified (and a ready explanation for the lack of success in the studies already referenced) is the relatively narrow window for absorption of the drug in the small intestine and the relatively short half life of the drug. Furthermore, the rapid elimination of amoxycillin (excretion half-life is 1.3 hours) makes it difficult to maintain serum levels as clearance from the body is very rapid.

In existing tablet formulations comprising amoxycillin and potassium clavulanate, amoxycillin is present in the form amoxycillin trihydrate, as the use of this form provides tablets with greater storage stability than those in which amoxycillin is present as sodium amoxycillin (see GB 2 005 538, Beecham Group Ltd). Sodium amoxycillin is however used as the amoxycillin component in existing formulations of amoxycillin and potassium clavulanate adapted for IV administration. The form of sodium amoxycillin used is a spray-dried form. In addition, EP 0 131 147-Al (Beecham Group plc) describes a further form of sodium amoxycillin, so-called "crystalline sodium amoxycillin". A further process for preparing salts of amoxycillin, including sodium amoxycillin, is described in WO 99/62910 (SmithKline Beecham). Sodium amoxycillin is relatively water soluble in comparison to amoxycillin trihydrate.

Formulations comprising clavulanic acid and a pharmaceutically acceptable organic acid or a salt-like derivative thereof, for example calcium citrate, have been described in WO 96/07408 (SmithKline Beecham). In such formulations, it is postulated that the presence of the calcium citrate would help suppress the gastrointestinal intolerance associated with oral dosing of clavulanate-containing products.

Furthermore, U.S. Pat. No. 5,051,262 (Elan Corp) describes the incorporation of an organic acid into a modified release formulation, to provide a microenvironment in which the locally modified pH helps to protect the active ingredient from degradation.

Of concern is the increasing resistance of pathogenic organisms, such as those found in respiratory tract infections, to anti-infective agents such as amoxycillin/potassium clavulanate, in particular drug resistant S pneumoniae. Increased resistance to penicillin of S pneumoniae (due to modified penicillin binding proteins) is developing around the world and is affecting clinical outcomes (see for instance Applebaum P C, Ped Inf Dis J, 1996, 15(10), 932–9). These penicillin resistant S pneumoniae (PRSP) have also been termed "DRSP" as they often exhibit decreased susceptibility not only to penicillin but also to a wider range of antimicrobial classes, including macrolides, azalides, beta-lactams, sulfonamides and tetracyclines. Amoxycillin (with or without clavulanate), along with some of the newer quinolones, has remained among the most active oral drugs against the increasingly resistant isolates of S pneumoniae, based on both MIC levels and pharmacokinetic properties of these compounds. Resistance rates (and MICs) have however continued to increase. Penicillin resistance in S. pneumoniae can be assessed according to criteria developed by the National Committee for Clinical Laboratory Standards (NCCLS), as follows: susceptible strains have MICs of $\leq 0.06$ µg/ml, intermediate resistance is defined as an MIC in the range 0.12 to 1.0 µg/ml while penicillin resistance is defined as an MIC of $\geq 2$ µg/ml. Furthermore, it is found that some 10% of pneumococci now have an amoxycillin MIC of 2 µg/ml.

There is consequently a need to provide new formulations of amoxycillin/clavulanate that combine the known safety profile and broad spectrum with improved activity against DRSP, including PRSP, with higher MICs in empiric treatment of respiratory infections where S. pneumoniae, H. influenzae and M. catarrhalis are likely pathogens.

For β-lactams, including amoxycillin, it is recognised that the time above minimum inhibitory concentration (T>MIC) is the pharmacodynamic parameter most closely related to efficacy. For a variety of β-lactams, a bacteriological cure rate of 85 to 100% is achieved when serum concentrations exceed the MIC for more than about 40% of the dosing interval (Craig and Andes, Ped Inf Dis J, 1996, 15, 255–259). For a 12 hour dosing interval, this is about 4.8 hours.

A further parameter which may be of importance is the ratio of the maximum plasma concentration ($C_{max}$) to the MIC value, as this may be related to the potential to select for resistance. Too low a ratio may encourage the development of resistant strains. Preferably, the plasma $C_{max}$ value is well above the MIC value, for instance, at least two times, more preferably at least three times, most preferably at least four times, the MIC value.

In a clinical study using the existing Augmentin 875/125 mg tablet, it was found that, when dosed at 12 hour intervals, the time above MIC was about 40% for an MIC of 2 µg/ml but only about 30% for an MIC of 4 µg/ml. The existing Augmentin 875/125 mg tablet has a $C_{max}$ value of 11.6±2.8 µg/ml (Physicians Desk Reference, Medical Economics Co, 52 edition, 1998, 2802).

Based on the foregoing considerations, there is a continuing need to provide new dosage regimens for amoxycillin/clavulanate giving optimised pharmacokinetic profiles for amoxycillin while not compromising the bioavailability of clavulanate, so that therapy is maximised, particularly against more resistant bacteria while the (further) development of resistance is minimised. It has now been found that such can be achieved using higher dosages of amoxycillin than previously contemplated.

Accordingly, in a first aspect, the present invention provides for a method of treating bacterial infections in humans which comprises orally administering thereto a therapeutically effective amount of amoxycillin and potassium clavulanate such that the amount of amoxycillin is in the range 1900 to 2600 mg, preferably 1950 to 2550 mg, and the amount of potassium clavulanate is such that the weight ratio of amoxycillin to clavulanate is from 2:1 to 20:1, preferably 7:1 to 20:1, more preferably 14:1 to 20:1, at intervals of about 12 hours (hereinafter "h").

Preferably, the dosage regimen provides a mean plasma concentration of amoxycillin of 4 µg/mL for at least 4.4 h, preferably at least 4.6 h, more preferably at least 4.8 h, most preferably for about 6 h or longer.

More preferably, the dosage regimen provides a mean plasma concentration of amoxycillin of 8 µg/ml for at least 4.4 h, more preferably at least 4.6 h, most preferably at least 4.8 h.

Preferably, the dosage regimen provides a mean maximum plasma concentration ($C_{max}$) of amoxycillin which is at least 8 µg/mL, preferably at least 12 µg/mL, yet more preferably at least 14 µg/mL, most preferably at least 16 µg/mL.

Preferably, the mean plasma concentration of amoxycillin and the mean maximum plasma concentration of amoxycillin are measured after oral administration of a formulation comprising amoxycillin at the start of a light meal.

In a further aspect, the present invention provides for a method of treating bacterial infections in humans which comprises administering thereto a therapeutically effective amount of amoxycillin and potassium clavulanate such that the amount of amoxycillin is in the range 1400 to 1900 mg, preferably 1500 to 1900 mg, and the amount of potassium clavulanate is such that the weight ratio of amoxycillin to clavulanate is from 2:1 to 14:1, preferably 7:1 to 14:1, more preferably 12:1 to 14:1, at intervals of about 12 h, such that the dosage regimen provides a mean plasma concentration of amoxycillin of 4 µg/mL for at least 4.4 h, preferably at least 4.6 h, more preferably at least 4.8 h, most preferably for about 6 h or longer; more preferably, a mean plasma concentration of amoxycillin of 8 µg/ml for at least 4.4 h, more preferably at least 4.6 h, most preferably at least 4.8 h, and a mean maximum plasma concentration ($C_{max}$) of amoxycillin which is at least 8 µg/mL, preferably at least 12 µg/mL, yet more preferably at least 14 µg/mL, most preferably at least 16 µg/mL.

Bacterial infections amenable to the present invention include infections caused by the organisms S pneumoniae (including Drug Resistant S. pneumoniae (DRSP), for instance Penicillin Resistant S. pneumoniae (PRSP)), and/or the β-lactamase producing respiratory pathogens, most notably H. influenzae and M. catarrhalis, such as respiratory tract infections, including community acquired pneumoniae (CAP), acute exacerbations of chronic bronchitis (AECB) and acute bacterial sinusitis (ABS), where the higher break points achievable through the improved pharmacokinetic profile will be especially advantageous compared to existing antibacterial agents. Most outpatient respiratory infections are caused by either S. pneumoniae and/or the β-lactamase producing bacteria and are treated empirically so there is a continuing need for a method of treatment, such as the present invention, that provides a spectrum of activity that covers all such pathogens. The duration of therapy will generally between 7 and 14 days, typically 7 days for indications such as acute exacerbations of chronic bronchitis but 10 days for acute bacterial sinusitis. Typically, the dosages regimens are designed for adult patients, rather than paediatric patients.

The term "amoxycillin" as used herein shall mean amoxycillin, or an alkaline salt thereof, in particular amoxycillin trihydrate and (crystallised) sodium amoxycillin, without distinction and unless otherwise indicated.

Unless otherwise indicated, weights of amoxycillin and (potassium) clavulanate refer to the equivalent weights of the corresponding free acids. In addition, it will be appreciated that in practice, weights of amoxycillin and clavulanate to be incorporated into a formulation will be further adjusted, in accord with conventional practice, to take account of the potency of the amoxycillin and clavulanate.

In a first embodiment, a dosage of amoxycillin of from 1900 to 2600 mg and a corresponding amount of potassium clavulanate may delivered from an immediate release formulation. Accordingly, in a further aspect, the present invention provides for method of treating bacterial infections in humans which comprises administering thereto a therapeutically effective amount of amoxycillin and potassium clavulanate such that the amount of amoxycillin is in the range 1900 to 2600, preferably 1950 to 2550 mg, and the amount of potassium clavulanate is such that the weight ratio of amoxycillin to clavulanate is from 2:1 to 20:1, preferably 7:1 to 20:1, more preferably 14:1 to 20:1, at intervals of about 12 h, wherein the dosage is delivered from an immediate formulation.

As used herein, the term "immediate release" shall mean the release of the majority of the active material content within a relatively short time, for example within 1 hour, preferably within 30 minutes, after oral ingestion. Examples of such immediate release formulations include conventional swallow tablets, dispersible tablets, chewable tablets, single dose sachets and capsules, or effervescent forms thereof.

Representative dosages include 2000/125, 2250/125 and 2500/125 mg of amoxycillin and potassium clavulanate, respectively. A preferred dosage is 2000/125 mg of amoxycillin and potassium clavulanate.

The dosage in an immediate release formulation may be provided as a single tablet, for instance a dispersible tablet, a chewable tablet which may also be, effervescent and/or dispersible, a single dose capsule or a single dosage sachet, comprising, for instance, 2000, 2250 or 2500 mg amoxycillin and 125 mg potassium clavulanate. Alternatively, the dosage may be made up of a number of smaller tablets or capsules, for instance, 2, 3 or 4, some of which may be the same and some of which may comprise amoxycillin only and no potassium clavulanate. Representative such smaller tablets include swallow tablets, dispersible tablets and chewable tablets which may also be effervescent and/or dispersible. Thus, for instance, a dosage of 2000 mg amoxycillin and 125 mg potassium clavulanate may be provided by a combination of three tablets each comprising 500 mg amoxycillin and one tablet comprising 500 mg amoxycillin and 125 mg potassium clavulanate. Alternatively, such a dosage may be provided by two tablets each comprising 1000/62.5 mg amoxycillin/potassium clavulanate. In addition, a dosage of 2250 mg amoxycillin and 125 mg potassium clavulanate may be provided by a combination of four tablets comprising 500 mg amoxycillin and one tablet comprising 250 mg amoxycillin and 125 mg potassium clavulanate or two tablets comprising 875 mg amoxycillin and one tablet comprising 500 mg amoxycillin and 125 mg potassium clavulanate. Furthermore, a dosage of 2500 mg amoxycillin and 125 mg potassium clavulanate may be provided by a combination of four tablet comprising 500 mg amoxycillin and one tablet comprising 500 mg amoxycillin and 125 mg potassium clavulanate. Tablets comprising 500 and 875 mg amoxycillin and 250/125, 500/125 and 875/125 mg amoxycillin/potassium clavulanate are already commercially available.

It will be appreciated that immediate release tablets comprising 1000/62.5 mg are novel. Accordingly, in a further aspect, the present invention provides for an immediate release pharmaceutical tablet formulation comprising 1000 mg +5% amoxycillin and 62.5 mg±5% potassium clavulanate, in a nominal ratio of about 16:1, in combination with pharmaceutically acceptable excipients or carriers. Immediate release tablets comprising 1000/62.5 mg can be readily prepared by adapting compositions previously described for 875/125 and 1000/125 mg tablets (see for instance, WO 95/28927 and WO 98/35672, SmithKline Beecham).

It will also be appreciated that immediate release single dosage sachets comprising 2000/125 mg, 2250/125 mg or 2500/125 mg, or the corresponding half quantities thereof, are novel. Accordingly, in a further aspect, the present invention provides for an immediate release pharmaceutical formulation in the form of a single dose sachet comprising 2000, 2250 or 2500 mg±5% amoxycillin and 125 mg±5% potassium clavulanate, in a nominal ratio of about 16:1, 18:1 or 20:1, respectively, or the corresponding half quantities thereof, in combination with pharmaceutically acceptable excipients or carriers. Such sachets can be readily prepared by adapting compositions previously described for 875/125 and 1000/125 mg sachets (see for instance, WO 92/19277 and WO 98/35672, SmithKline Beecham).

It will be further appreciated that immediate release chewable tablets comprising 2000, 2250 or 2500/125 mg are novel. Accordingly, in a further aspect, the present invention provides for an immediate release pharmaceutical formulation in the form of a chewable, optionally effervescent, tablet comprising 2000, 2250, or 2500 mg amoxycillin and 125 mg±5% potassium clavulanate, in a nominal ratio of about 16:1, 18:1 or 20:1, respectively, or the corresponding half quantities thereof, in combination with a chewable base and, if effervescent, an effervescent couple, and other pharmaceutically acceptable excipients or carriers. Such chewable tablets can be readily prepared by adapting compositions previously described for chewable tablets comprising amoxycillin and potassium clavulanate (see for instance, EP-A-0 396 335, Beecham Group and WO 98/35672, SmithKline Beecham).

In a second embodiment, a dosage of amoxycillin of from 1900 to 2600 mg and a corresponding amount of potassium clavulanate may be delivered from a modified release formulation. Accordingly, in a further aspect, the present invention provides for method of treating bacterial infections in humans which comprises administering thereto a therapeutically effective amount of amoxycillin and potassium clavulanate such that the amount of amoxycillin is in the range 1900 to 2600 mg, preferably 1950 to 2550 mg, and potassium clavulanate is present in a pro rata amount such that the weight ratio of amoxycillin to potassium clavulanate is from 2:1 to 20:1, preferably 7:1 to 20:1, more preferably 14:1 to 20:1, at intervals of about 12 h, in which the dosage is delivered from a modified release formulation.

In a third embodiment, a dosage of amoxycillin of from 1400 to 1900 mg and a corresponding amount of clavulanate may be delivered from the modified release formulation. Accordingly, in a further aspect, the present invention provides for method of treating bacterial infections in humans which comprises administering thereto a therapeutically effective amount of amoxycillin and potassium clavulanate such that the amount of amoxycillin is in the range 1400 to 1900 mg, preferably 1500 to 1900 mg, and potassium clavulanate is present in a pro rata amount such that the weight ratio of amoxycillin to clavulanate is from 2:1 to 14:1, preferably 7:1 to 14:1, more preferably 12:1 to 14:1, at intervals of about 12 h, in which the dosage is delivered from a modified release formulation.

As used herein, the term "modified release" shall mean the release of a drug substance from a pharmaceutical formulation which is at a slower rate than from an immediate release formulation such as a conventional swallow tablet or capsule. The modified release formulation may include both an immediate release portion or phase and a slow release portion or phase. Modified release formulations are well known in the art, see for instance Remington: The Science and Practice of Pharmacy, Nineteenth Edn, 1995, Mack Publishing Co, Pennsylvania, USA, whose disclosure is incorporated herein by reference.

Preferably, the modified release formulations of the present invention are formulated such that the release of amoxycillin is effected predominantly through the stomach and small intestine, so that absorption through the specific amoxycillin absorption site in the small intestine is maximised. Preferably, the amoxycillin release profile is made up of a contribution from an immediate release component which is then complemented and extended by an on-going contribution from a slow release component. Preferably, potassium clavulanate is released substantially immediately from the formulation, when the formulation reaches the stomach and is absorbed therefrom, thereby minimising the risk of degradation from prolonged exposure to the stomach. Such formulations are preferably formulated such that the release of amoxycillin and potassium clavulanate occurs predominantly within 3 hours of ingestion of the formulation.

Typically, a dosage will provide 125 mg of potassium clavulanate, the amount approved in existing regimens where a lesser amount of amoxycillin is administered.

Representative modified release dosages include 1500/125, 1750/125 and 2000/125 mg of amoxycillin and potassium clavulanate, respectively. A preferred dosage is 2000/125 mg of amoxycillin and potassium clavulanate.

The dosage in a modified release formulation may conveniently be provided as a number of swallow tablets or capsules, for instance two, three or four, some of which may be the same and some of which may comprise amoxycillin only and no potassium clavulanate. Thus, for instance, a dosage of 2000 mg amoxycillin and 125 mg potassium clavulanate may be provided by two tablets each comprising 1000/62.5 mg amoxycillin/potassium clavulanate, one tablet comprising 1000 mg of amoxycillin and one tablet comprising 1000/125 mg amoxycillin/potassium clavulanate, two tablets each comprising 500 mg amoxycillin and one tablet comprising 1000/125 mg amoxycillin/potassium clavulanate or four tablets each comprising tablet 500/32.25 mg amoxycillin/potassium clavulanate. In addition, a dosage of 1750 mg amoxycillin and 125 mg potassium clavulanate may be provided by two tablets each comprising 875/62.5 mg amoxycillin/potassium clavulanate or one tablet comprising 875 mg of amoxycillin and one tablet comprising 875/125 mg amoxycillin/potassium clavulanate. A preferred tablet comprises 1000/62.5 mg amoxycillin/potassium clavulanate.

The dosage in an modified release formulation may be may also provided as a single tablet. Because of the quantities of drug substance being used, this would preferably be other than a swallow tablet, for instance a dispersible tablet or a chewable tablet which may also be effervescent and/or dispersible or a dispersible tablet. A single unit dosage may also be conveniently provided as a single dosage sachet. It will be appreciated that the dosage may also be provided as a number of smaller non-swallow tablets or sachets, for instance 2×1000/62.5 mg or 4×500/32.25 mg amoxycillin/potassium clavulanate.

Preferably, in the modified release formulation, all the potassium clavulanate is provided in an immediate release phase while amoxycillin is provided in both an immediate release and a slow release phase.

Accordingly, in a further aspect, the present invention provides for a modified release pharmaceutical formulation comprising amoxycillin and potassium clavulanate in the ratio from 2:1 to 20:1, preferably 7:1 to 20:1, more preferably 12:1 to 20:1, most preferably 14:1 to 16:1 in which all of the potassium clavulanate and a first part of amoxycillin are formulated with pharmaceutically acceptable excipients which allow for immediate release of the potassium clavulanate and the first part of amoxycillin, to form an immediate release phase, and further comprising a second part of amoxycillin formulated with pharmaceutically acceptable excipients which allow for slow release of the second part of amoxycillin, to form a slow release phase.

As used herein, the term "slow release" refers to the gradual but continuous or sustained release over a relatively extended period of the active material content (in this case amoxycillin) after oral ingestion and which starts when the formulation reaches the stomach and starts to disintegrate/dissolve. The release will continue over a period of time and may continue through until and after the formulation reaches the intestine. This can be contrasted with the term "delayed release" in which release of the active does not start immediately the formulation reaches the stomach but is delayed for a period of time, for instance until when the formulation reaches the intestine when the increasing pH is used to trigger release of the active from the formulation.

Preferably, the modified release formulation has an in vitro dissolution profile in which 45 to 65%, preferably 45 to 55% of the amoxycillin content is dissolved within 30 min; further in which 50 to 75%, preferably 55 to 65% of the amoxycillin content is dissolved within 60 min; further in which 55 to 85%, preferably 60 to 70% of the amoxycillin content is dissolved within 120 min; further in which 70 to 95%, preferably 75 to 85% of the amoxycillin content is dissolved within 180 min; and further in which 70 to 100%, preferably 75 to 100% of the amoxycillin content is dissolved within 240 min. In comparison, a conventional, immediate release amoxycillin tablet dissolves essentially completely within 30 minutes. The dissolution profile may be measured in a standard dissolution assay, for instance <711> Dissolution Test, Apparatus 2, provided in USP 23, 1995, at 37.0±0.5° C., using deionised water (900 mL) and a paddle speed of 75 rpm.

Preferably, the modified release formulation has a biphasic profile in vivo with respect to amoxycillin, that is an initial burst from the immediate release phase to provide an acceptable $C_{max}$ value, supplemented by a further contribution from the slow release phase, to extend the T>MIC parameter to an acceptable value.

Preferably, the modified formulation provides an "Area Under the Curve" (AUC) value which is substantially similar to, for instance at least 80%, preferably at least 90%, more preferably about 100%, of that of the corresponding dosage of amoxycillin taken as a conventional (immediate release) formulation, over the same dosage period, thereby maximising the absorption of the amoxycillin component from the slow release component.

The pharmcokinetic profile for a dosage of the present invention may be readily determined from a single dosage bioavailability study in human volunteers. Plasma concentrations of amoxycillin may then be readily determined in blood samples taken from patients according to procedures well known and documented in the art.

Representative modified release formulations include a tablet, including swallow tablets, dispersible tablets, chewable tablets which may also be effervescent and/or dispersible and, a capsule, granules or a sachet, typically a swallow tablet.

Representative modified release formulations having an immediate and a slow release phase provide a unit dosage in the range 700 to 1300 mg, preferably, 950 to 1300 mg, amoxycillin, for instance unit dosages of 1000, 875 and 750/62.5 mg amoxycillin/clavulanate. Alternatively, and where the physical size of the dosage form is not a problem, the unit dosage may provide the whole dosage, for instance a single dosage sachet, chewable tablet or dispersible tablet may comprise 1400 to 2600 mg, preferably, 1900 to 2600 mg, amoxycillin, for instance unit dosages of 2000, 1750 and 1500/125 mg amoxycillin/clavulanate. It will be appreciated that such 1000, 875 and 750/62.5 mg formulations are novel.

Accordingly, in a further aspect, the present invention provides for a pharmaceutical formulation having an immediate release phase and a slow release phase and comprising:

(a) a unit dosage in the range 700 to 1300 mg, preferably, 950 to 1300 mg, amoxycillin, and a corresponding amount of potassium clavulanate, in a nominal ratio of about 16:1, 14;1 or 12:1, for instance unit dosages of 1000, 875 or 750 mg±5% amoxycillin and 62.5 mg±5% potassium clavulanate, respectively, or (b) a unit dosage in the range 1400 to 2600 mg, preferably, 1900 to 2600 mg, amoxycillin, and a corresponding amount of potassium clavulanate, in a nominal ratio of about 16:1, 14;1 or 12:1, for instance unit dosages of 2000, 1750 or 1500 mg±5% amoxycillin and 62.5 mg±5% potassium clavulanate, respectively, in combination with pharmaceutically acceptable excipients or carriers.

Preferably, the ratio of amoxycillin in the immediate and slow release phases is from 3:1 to 1:3, more preferably, from 2:1 to 2:3, yet more preferably 3:2 to 1:1. Representative ratios include about 2:1, 9:7 or 1:1. It is found useful to employ an excess of amoxycillin in the immediate release phase, to ensure an adequate $C_{max}$ value.

In the modified release formulations of the present invention, the portion of amoxycillin which is released immediately may be provided as amoxycillin trihydrate or an alkaline salt thereof, for instance potassium or sodium amoxycillin, preferably, (crystallised) sodium amoxycillin or a mixture thereof, preferably amoxycillin trihydrate; while the portion of amoxycillin which is released slowly is provided as amoxycillin trihydrate or an alkaline salt thereof, for instance potassium or (crystallised) sodium amoxycillin or a mixture thereof, preferably (crystallised) sodium amoxycillin.

Preferably, the modified release formulation is a tablet. In a preferred modified release tablet comprising 1000 mg amoxycillin and 62.5 mg potassium clavulanate, the immediate release phase comprises about 563 mg±5% amoxycillin trihydrate and about 62.5 mg±5% of potassium clavulanate and the slow release phase about 438 mg±5% of amoxycillin, preferably as (crystallised) sodium amoxycillin.

In a representative modified release tablet of the present invention, the immediate release phase comprises about 438 mg amoxycillin, preferably amoxycillin trihydrate and about 62.5 mg of potassium clavulanate and the slow release phase about 438 mg of amoxycillin, preferably (crystallised) sodium amoxycillin, providing overall an 875/62.5 mg (14:1) tablet.

In a further representative tablet of the present invention, the immediate release phase comprises about 500 mg amoxycillin and about 62.5 mg of potassium clavulanate and the slow release phase about 250 mg of amoxycillin, preferably (crystallised) sodium amoxycillin, providing overall a 750/62.5 mg (12:1) tablet.

It will be appreciated that the use of a mixture of amoxycillin trihydrate and sodium amoxycillin is more generally applicable to other pharmaceutical formulations comprising amoxycillin and potassium clavulanate.

Accordingly, in a further aspect, the present invention provides for a pharmaceutical formulation comprising amoxycillin and potassium clavulanate in a ratio of from 1:1 to 30:1, preferably 2:1 to 20:1, more preferably 12:1 to 20:1, yet more preferably 14:1 to 16:1, in which amoxycillin is provided as a mixture of amoxycillin trihydrate and sodium amoxycillin in a ratio of from 3:1 to 1:3, more preferably from 2:1 to 2:3, yet more preferably 3:2 to 1:1. Preferably, sodium amoxycillin is crystallised sodium amoxycillin. Representative formulation types include tablets, including immediate release and modified release tablets as herein described, as well as other solid dosage forms such as capsules, single dosage sachets and granules. Representative tablets include those comprising 1000, 875, 500 and 250 mg amoxycillin and a corresponding weight of potassium clavulanate. Representative ratios include 4:1, 7:1, 8:1, 14:1, and 16:1 (amoxycillin:clavulanate). Preferably, in modified release formulations of the present invention, the amoxycillin in the immediate release phase consists essentially of amoxycillin trihydrate and the amoxycillin of the slow release phase consists essentially of sodium amoxycillin.

For a tablet formulation, the immediate and slow release phases may be provided in a number of different formats.

In a preferred aspect, the immediate and slow release phases are provided as separate layers of a layered tablet.

Accordingly, in a further aspect, the present invention provides for a layered tablet formulation comprising potassium clavulanate and amoxycillin in an immediate release layer phase and amoxycillin in a slow release layer. The layered tablet may have two layers, or two layers plus one or more barrier layer, as well as a coating layer. As used herein, the term "bilayer" tablet refers to a tablet consisting of an immediate release and a slow release layer, optionally with a coating layer.

An immediate release layer may be, for example, a layer which disintegrates immediately or rapidly and has a composition similar to that of known tablets which disintegrate immediately or rapidly. For example, the layer may comprise, in addition to the active material content, excipients including diluents such as microcrystalline cellulose; disintegrants such as cross-linked polyvinylpyrrolidone (CLPVP), sodium starch glycollate; compression aids such as colloidal silicon dioxide and microcrystalline cellulose; and lubricants such as magnesium stearate. Such an immediate release layer may comprise around 60 to 85% (all percentages given herein are on a weight percentage basis unless otherwise stated), preferably 70 to 85%, of active material content, around 10 to 30%, preferably 10 to 20% of fillers/compression aids, and conventional amounts of disintegrants and lubricants, typically about 0.5 to 3%, etc.

An alternative type of immediate release layer may be a swellable layer having a composition which incorporates polymeric materials which swell immediately and extensively in contact with water or aqueous media, to form a water permeable but relatively large swollen mass. Active material content may be immediately leached out of this mass.

Slow release layers have a composition which comprises amoxycillin together with a release retarding excipient which allows for slow release of amoxycillin. Suitable release retarding excipients include pH sensitive polymers, for instance polymers based upon methacrylic acid copolymers such as the Eudragit (trade mark) polymers, for example Eudragit L (trade mark) which may be used either alone or with a plasticiser; release-retarding polymers which have a high degree of swelling in contact with water or aqueous media such as the stomach contents; polymeric materials which form a gel on contact with water or aqueous media; and polymeric materials which have both swelling and gelling characteristics in contact with water or aqueous media.

Release retarding polymers which have a high degree of swelling include, inter alia, cross-linked sodium carboxymethylcellulose, cross-linked hydroxypropylcellulose, high-molecular weight hydroxypropylmethylcellulose, carboxymethylamide, potassium. methacrylatedivinylbenzene co-polymer, polymethylmethacrylate, cross-linked polyvinylpyrrolidone, high-molecular weight polyvinylalcohols etc.

Release retarding gellable polymers include methylcellulose, carboxymethylcellulose, low-molecular weight hydroxypropylmethylcellulose, low-molecular weight polyvinylalcohols, polyoxyethyleneglycols, non-cross linked polyvinylpyrrolidone, xanthan gum etc.

Release retarding polymers simultaneously possessing swelling and gelling properties include medium-viscosity hydroxypropylmethylcellulose and medium-viscosity polyvinylalcohols.

A preferred release-retarding polymer is xanthan gum, in particular a fine mesh grade of xanthan gum, preferably pharmaceutical grade xanthan gum, 200 mesh, for instance the product Xantural 75 (also known as Keltrol CR, Trade Mark, Monsanto, 800 N Lindbergh Blvd, St Louis, Mo. 63167, USA). Xanthan gum is a polysaccharide which upon hydration forms a viscous gel layer around the tablet through which the active has to diffuse. It has been shown that the smaller the particle size, the slower the release rate. In addition, the rate of release of drug substance is dependent upon the amount of xanthan gum used and can be adjusted to give the desired profile. Controlled release formulations comprising from 7.5 to 25% xanthan gum are described in EP 0 234 670-A (Boots Co plc). The preferred embodiment is a tablet comprising ibuprofen as the drug substance and 15–20% xanthan gum, which is taken once daily.

Examples of other polymers which may be used include Methocel K4M (Trade Mark), Methocel E5 (Trade Mark), Methocel E50 (Trade Mark), Methocel E4M (Trade Mark), Methocel K15M (Trade Mark) and Methocel K100M (Trade Mark). An example of a suitable polymer mixture is a mixture of Methocel E5 and K4M, for example 1:1, w:w.

Other known release-retarding polymers which may be incorporated include hydrocolloids such as natural or synthetic gums, cellulose derivatives other than those listed above, carbohydrate-based substances such as acacia, gum tragacanth, locust bean gum, guar gum, agar, pectin, carageenin, soluble and insoluble alginates, carboxypolymethylene, casein, zein, and the like, and proteinaceous substances such as gelatin.

Such a slow release layer may contain polymers which immediately swell in contact with water or aqueous media so that they form a relatively large swollen mass which is not immediately discharged from the stomach into the intestine.

The slow release layer may also include diluents such as lactose; compression aids such as microcrystalline cellulose; and lubricants such as magnesium stearate. The slow release layer may further comprise disintegrants, such as cross-linked polyvinylpyrrolidone (CLPVP) and sodium starch glycollate; binders such as povidone (polyvinylpyrrolidone); desiccants, such as silicon dioxide; and soluble excipients such as mannitol or other soluble sugars. Typically, the slow release layer comprises from about 60 to 80% by weight of amoxycillin; from 10 to 20% by weight of diluent/compression aid and from 1 to 2.5% by weight of lubricant.

When xanthan gum is used as release-retarding polymer, the layer contains from 60 to 80% of amoxycillin, from 1 to 25%, preferably 2 to 15%, more preferably 4 to 15% of xanthan gum, from 10 to 30%, preferably 10 to 20% of fillers/compression aids, and conventional quantities of lubricants, all % being by weight of the layer. In a preferred embodiment, the slow release layer comprises from 70 to 80% of amoxycillin, from 4 to 10%, of xanthan gum, from 10 to 20% of microcrystalline cellulose, and from 1 to 2.5% of magnesium stearate, all % being by weight of the layer.

When release-retarding polymers other than xanthan gum are used, the slow release layer may contain around 30 to 70%, preferably from 40 to 60%, of amoxycillin, from 15 to 45% of release-retarding polymer, from 0 to 30% of fillers/compression aids, conventional quantities of lubricants, and from 5 to 20% of soluble excipients, all % being by weight of the layer.

It has also been surprisingly found that when the amoxycillin in the slow release layer is in the form of a soluble salt thereof, such as sodium amoxycillin, then the release thereof may be retarded by the inclusion of an organic acid.

Accordingly, in a further aspect, the present invention provides for the use of a pharmaceutically acceptable organic acid as a release retarding excipient in a formulation comprising a pharmaceutically acceptable soluble salt of amoxycillin, for instance sodium or potassium amoxycillin, preferably sodium amoxycillin.

It will be appreciated that the use of an organic acid as a release retarding excipient is more generally applicable beyond the particular formulations hereinbefore described.

Accordingly, the present invention further provides for a pharmaceutical formulation comprising a pharmaceutically acceptable soluble salt of amoxycillin, for instance sodium amoxycillin, in a slow release phase which further comprises a release retarding excipient which is a pharmaceutically acceptable organic acid present in a molar ratio of from 100:1 to 1:10 preferably 50:1 to 1:5, more preferably 20:1 to 1:2 (amoxycillin to organic acid).

It is believed that intimate contact between the organic acid and the salt of amoxycillin in the pharmaceutical formulation, for instance as a consequence of compacted granule formation or direct compression in a tablet, causes some form of interaction which modifies the release of the amoxycillin component from the formulation.

Soluble pharmaceutically acceptable salts of amoxycillin include alkali metal salts such as sodium and potassium; alkaline earth metal salts such as magnesium and calcium, and acid salts such as amoxycillin hydrochloride. Preferably, the salt is sodium amoxycillin, more preferably crystalline sodium amoxycillin.

As used herein, the term "pharmaceutically acceptable organic acid" shall mean organic acids which are without pharmacological effect per se, have acceptable organoleptic properties, have acceptable density, do not have an extreme pH and are preferably solid. Examples thereof include mono-carboxylic acids and poly-carboxylic acids having from 2 to 25, preferably from 2 to 10, carbon atoms; monocyclic and polycyclic aryl acids such as benzoic acid; as well as monohydrogen, dihydrogen etc metal salts of multi-valent acids. A single pharmaceutically acceptable organic acid may be used, or two or more of such may be used in combination. Preferably, the organic acid is a $C_{(2-10)}$alkyl- or alkenyl-carboxylic acid having from one, two or three carboxylic acid groups, and optionally with one or more hydroxy substituents or an additional CO group in the carbon chain, for instance malonic acid, succinic acid, fumaric acid, maleic acid, adipic acid, lactic acid, levulinic acid, sorbic acid or a fruit acid such as tartaric acid, malic acid, ascorbic acid or citric acid, or an acidic salt thereof, more preferably anhydrous citric acid.

The organic acid may be used alone or in combination with a release retarding polymer as hereinbefore described. A preferred combination comprises citric acid and a release retarding gellable polymer, in particular xanthan gum. In the presence of the organic acid, for instance citric acid, xanthan gum may be used at a lower level then when included on its own, for instance, from 0.5 to 8%, preferably 1 to 5%, typically about 2%, by weight of the slow release layer.

When an organic acid is used as a release-retarding excipient, the slow release layer contains from 60 to 80% of a soluble salt of amoxycillin, from 10 to 30%, preferably 10 to 20% of fillers/compression aids, and conventional quantities of lubricants, all % being by weight of the layer. In a preferred embodiment, the slow release layer comprises from 60 to 70% of a soluble salt of amoxycillin, from 10 to 20% of microcrystalline cellulose, and from 1 to 2.5% of magnesium stearate, all % being by weight of the layer.

In a representative example, a layered tablet comprises in the slow release layer crystallised sodium amoxycillin and citric acid, in a molar ratio of about 50:1 to 1:2, preferably 20:1 to 1:2, more preferably 2:1 to 1:1.2, yet more preferably about 1:1. In a preferred embodiment, the slow release layer comprises about 438 mg±5% crystallised sodium amoxycillin, about 78 mg±10% citric acid and about 2% by weight of xanthan gum.

In a preferred layered tablet comprising 1000 mg amoxycillin and 62.5 mg potassium clavulanate, the immediate release layer comprises about 563 mg±5% amoxycillin, preferably amoxycillin trihydrate, and about 62.5 mg±5% of potassium clavulanate and the slow release layer about 438 mg±5% of amoxycillin, preferably crystallised sodium amoxycillin, about 78 mg±10% citric acid and about 2% by weight of xanthan gum.

The tablet formulations of the invention may also include one or more barrier layers, which may be located between the respective first and second layers, and/or on one or more of the outer surfaces of the first and second layers, for example the end faces of the layers of a substantially cylindrical tablet. Such barrier layers may, for example, be composed of polymers which are either substantially or completely impermeable to water or aqueous media, or are slowly erodable in water or aqueous media or biological liquids and/or which swell in contact with water or aqueous media. Suitably the barrier layer should be such that it retains these characteristics at least until complete or substantially complete transfer of the active material content to the surrounding medium.

Suitable polymers for the barrier layer include acrylates, methacrylates, copolymers of acrylic acid, celluloses and derivatives thereof such as ethylcelluloses, cellulose acetate propionate, polyethylenes and polyvinyl alcohols etc. Barrier layers comprising polymers which swell in contact with water or aqueous media may swell to such an extent that the swollen layer forms a relatively large swollen mass, the size of which delays its immediate discharge from the stomach into the intestine. The barrier layer may itself contain active material content, for example the barrier layer may be a slow or delayed release layer. Barrier layers may typically have an individual thickness of 2 mm to 10 microns.

Suitable polymers for barrier layers which are relatively impermeable to water include the Methocel (trade mark) series of polymers mentioned above, for example Methocel K100M, Methocel K15M, Methocel E5 and Methocel E50, used singly or combined, or optionally combined with an Ethocel (trade mark) polymer. Such polymers may suitably be used in combination with a plasticiser such as hydrogenated castor oil. The barrier layer may also include conventional binders, fillers, lubricants and compression acids etc such as Polyvidon K30 (trade mark), magnesium stearate, and silicon dioxide, e.g. Syloid 244 (trade mark).

The tablet formulation of the invention may be wholly or partly covered by a coating layer, which may be a protective layer to prevent ingress of moisture or damage to the tablet. The coating layer may itself contain active material content, and may, for example, be an immediate release layer, which immediately disintegrates in contact with water or aqueous media to release its active material content, for example amoxycillin and potassium clavulanate. Preferred coating materials comprise hydroxypropylmethylcellulose and polyethylene glycol, with titanium dioxide as an opacifying agent, for instance as described in WO 95/28927 (SmithKline Beecham).

As well as active material content etc, the tablet of the invention may also include a pH modifying agent, such as a pH buffer, which may be contained in either the immediate-, or slow-release layers, or in a coating around all or part of the tablet. A suitable buffer is calcium hydrogen phosphate.

In a tablet without a barrier layer, the immediate release layer comprises from 50 to 60% and the slow release layer comprises from 40 to 50% of the overall tablet weight. When a barrier layer is present, the immediate release layer typically comprises from 40 to 50%, the slow release layer comprises from 35 to 45%, and the barrier layer comprises from 5 to 20% of the overall tablet weight.

It is found that a satisfactory pharmacokinetic profile may be obtained from a bilayered tablet of the present invention without the need to include a barrier layer. Accordingly, a bi-layer tablet is preferred. This also reduces the complexity of the manufacturing process.

It will be appreciated that 1000, 875 and 750/62.5 mg layered tablets having an immediate release layer and a slow release layer are novel. Accordingly, in a further aspect, the present invention provides for a pharmaceutical layered tablet formulation comprising an immediate release layer and a slow release layer and comprising from 700 to 1250 mg amoxycillin and a pro rata amount of potassium clavulanate, preferably 1000, 875 or 750 mg±5% amoxycillin and 62.5 mg±5% potassium clavulanate, in a nominal ratio of about 16:1, 14:1 or 12:1, respectively, in combination with pharmaceutically acceptable excipients or carriers. Preferably, the layered tablet is a bi-layered tablet.

Suitably the tablet formulations of the invention may be formed by known compression tabletting techniques, for example using a known multi-layer tabletting press. Preferably, in a preliminary step, slugging or roller compaction is used to form granulates. Lubricants and compression aids (if used) are then added, to form a compression blend for subsequent compaction.

Preferred bilayer tablets of the present invention may be made by a process which comprises, as an early phase, the formation of slow release compacted granules, comprising the steps of milling sodium amoxycillin, a portion of the diluent/compression aid such as microcrystalline cellulose (typically about 30%), a portion of the lubricant (typically about 70%) and a pharmaceutically acceptable organic acid such as a fruit acid, for instance citric acid, and then blending with a release retarding polymer such as xanthan gum, if present, and a compression aid such as colloidal silicon dioxide, compacting the blend, for instance in a roller compactor or by slugging, and then milling, to form slow release granules. Preferably such granules have a size in the range 100 to 1000 microns. The incorporation of xanthan gum appears to also have an unexpected benefit on processibility.

Such slow release compacted granules may then be blended with other excipients such as the remaining magnesium stearate and microcrystalline cellulose, to form a slow release compression blend.

In addition, amoxycillin trihydrate, potassium clavulanate (preferably as as 1:1 blend with microcrystalline cellulose), microcrystalline cellulose (a portion of total used), are milled and blended with a lubricant such as magnesium stearate (preferably about 50% f total), and then compacted, for instance in a roller compactor or by slugging, and milled to form immediate release compacted granules. These immediate release compacted granules may then be blended with other excipients such as the remaining magnesium stearate and microcrystalline cellulose (about 13%), a compression aid such as colloidal silica, and a disintegrant such as sodium starch glycollate, to form an immediate release compression blend.

The immediate release and slow release compression blends may then be compressed as separate layers on a bilayer tablet press, to form bilayer tablets.

Such slow release granules are novel. Accordingly, in a further aspect, the present invention provides for compacted granules comprising a soluble salt of amoxycillin, for instance sodium amoxycillin, a diluent/compression aid, and an organic acid or a release retarding polymer or a mixture thereof, as hereinbefore defined. In a yet further aspect, the present invention also provides for compacted granules comprising amoxycillin trihydrate, a diluent/compression aid, and a release retarding polymer, as hereinbefore defined Alternatively, a dry densification process may be used, e.g. briquetting. Typically the active material content, pH modifiers, buffers, fillers and/or diluent, release retarding agents, disintegrants and binders, when used are mixed, then lubricants and compression aids are added. The complete mixture may then be compressed under high pressure in the tablet press. A wet granulation process may be also be used, for instance with isopropanol as the solvent and Polyvidon K-30 (trade mark) as the wet granulating aid.

A barrier layer, if present, may typically be made up by a wet granulation technique, or by dry granulation techniques such as roller compaction. Typically the barrier material, e.g. Methocel (trade mark) is suspended in a solvent such as ethanol containing a granulation acid such as Ethocel or Polyvidon K-30 (trade mark), followed by mixing, sieving and granulation. Typically a first layer may be formed, then a barrier layer deposited upon it, e.g. by compression, spraying or immersion techniques, then the second layer may be formed so that the barrier layer is sandwiched between the first and second layers. Additionally, or alternatively, the first and second layers may be formed and a barrier layer may then be formed, for instance by compression, spraying or immersion, on one or more of the end faces of the tablet.

A process for the preparation of crystallised sodium amoxycillin is described in EP-A-0 131 147 (Beecham Group plc).

Potassium clavulanate is known to be extremely water sensitive. Therefore tablet formulations which contain potassium clavulanate should be made up in dry conditions, preferably at 30% relative humidity or less, and the ingredients of the formulation should be pre-dried where appropriate. Tablet formulations of the invention should be stored in containers which are sealed against the ingress of atmospheric moisture.

Tablet cores may then be coated with a coating layer which may be applied form an aqueous or an organic solvent system, preferably an aqueous solvent system, to provide film coated tablets.

The invention also provides a method for the manufacture of a tablet formulation as described above comprising the steps of forming said first and second layers, and any barrier layers and coating layer(s) which may be present.

In addition to the layered tablet approach hereinbefore described, other types of tablet may be used to provide an immediate release phase and a slow release phase, using the excipients hereinbefore described but providing the phases in different formats. Thus, the slow release phase may form the core of a tablet which is then surrounded by an outer casing forming the immediate release phase, optionally with an intermediate coating layer around the core and/or a final coating layer around the outer casing (see WO 95/28148, SmithKline Beecham). The slow release phase may also be provided as granules which are dispersed in a matrix of amoxycillin and potassium clavulanate, the matrix forming the immediate release phase (see WO 96/04908, SmithKline Beecham).

In a further variant, a monolith modified release tablet may be prepared from slow release compacted granules comprising amoxycillin, a diluent/compression aid such as microcrystalline cellulose, and a pharmaceutically acceptable organic acid such as a fruit acid, for instance citric acid (if amoxycillin is present as a soluble salt thereof), or a release retarding polymer such as xanthan gum or a mixture thereof, preferably a release retarding polymer (as hereinbefore described); and immediate release compacted granules comprising amoxycillin and potassium clavulanate (as hereinbefore described) or immediate release compacted granules comprising amoxycillin and potassium clavulanate, for instance in a 2:1 ratio, and further immediate release compacted granules comprising amoxycillin (as described in WO 98/35672, SmithKline Beecham Laboratoires Pharmaceutiques), the granules being combined with extragranular excipients to form tablets. Such granules may also be processed into other pharmaceutical formulations, for instance single dosage sachets, capsules or chewable tablets comprising a unit dosage as hereinbefore described.

Chewable tablets according to the present invention typically comprise a chewable base formed from, for instance, mannitol, sorbitol, dextrose, fructose or lactose alone or in combination. A chewable tablet may also comprise further excipients, for instance, disintegrants, lubricants, sweetening agents, colouring and flavouring agents. Such further excipients together will preferably comprise from 3 to 10%, more preferably 4 to 8%, yet more preferably 4 to 7% by weight of the tablet. Disintegrants may be present in from 1 to 4%, preferably from 1 to 3%, more preferably from 1 to 2% by weight of the tablet. Representative disintegrants include crospovidone, sodium starch glycollate, starches such as maize starch and rice strach, croscarmellose sodium and cellulose products such as microcrystalline cellulose, microfine cellulose, low substituted hydroxy propyl cellulose, either used singly or in admixture. Preferably, the disintegrant is crospovidone. Lubricants may be present in from 0.25 to 2.0%, preferably from 0.5 to 1.2% by weight of the tablet. Preferred lubricants include magnesium stearate. Preferably, the sweetening agent is an artificial sweetening agent such as sodium saccharin or aspartame, preferably aspartame, which may be present in from 0.5 to 1.5% by weight of the tablet. Preferably, a tablet of the present invention is substantially free of sugar (sucrose). Preferred flavouring agents include fruit flavours which may be natural or synthetic, for instance peppermint, cherry and banana, or a mixture thereof.

Single dose sachets according to the present invention comprise, in addition to the drug substance, excipients typically included in a sachet formulation, such as a sweetener, for instance aspartame, flavourings, for instance fruit flavours, optionally a suspending agent such as xanthan gum, as well as silica gel, to act as a desiccant.

Capsules according to the present invention comprise, in addition to the drug substance, excipients typically included in a capsule, for instance starch, lactose, microcrystalline cellulose, magnesium stearate. It will be appreciated that due to the hygroscopic nature of clavulanate, the use of materials such as gelatin for forming the capsules should be avoided. Preferably, capsules are prepared from materials such as HPMC or a gelatin/PEG combination.

In a further embodiment, the slow release phase may be provided as a separate component, for instance as a separate tablet, so that the unit dosage is provided as a combination of a conventional component in which amoxycillin and potassium clavulanate are released immediately, optionally with a conventional amoxycillin formulation such as a tablet, and a further formulation, for instance a tablet, comprising amoxycillin (and no potassium clavulanate) from which amoxycillin is released slowly. The weight of potassium clavulanate and the combined weights of amoxycillin in the conventional and slow release formulations will provide the overall unit dosage. Thus, for instance a dosage of 2000/125 mg may be provided by a combination of an existing 500/125 mg amoxycillin/potassium clavulanate tablet and a 500 mg amoxycillin tablet in combination with a slow release tablet comprising 1000 mg of amoxycillin. Furthermore, a dosage of 1750/125 mg may be provided by an existing 875/125 mg tablet (as described in WO 95/28927, SmithKline Beecham) in combination with a slow release tablet comprising 875 mg of amoxycillin. In addition, a dosage of 1500/125 mg may be provided by an existing 500/125 mg tablet and an existing 500 mg tablet of amoxycillin in combination with a slow release tablet comprising 500 mg of amoxycillin. Accordingly, in a further aspect, the present invention provides for a kit comprising a conventional (immediate release) tablet comprising amoxycillin and potassium clavulanate, optionally with a conventional (immediate release) tablet comprising amoxycillin, and a slow release tablet comprising amoxycillin (and no potassium clavulanate).

In a further aspect, the present invention provides for a pharmaceutical formulation, preferably a tablet, comprising amoxycillin (as the sole active ingredient) formulated with a release retarding excipient which causes a slow release of the amoxycillin from the formulation, and excluding; tablets which comprise 750 mg or less of amoxycillin in which the amoxycillin is present essentially as amoxycillin trihydrate; or tablets comprising from 400 to 500 mg amoxycillin in which amoxycillin is present as a mixture comprising at least 70% amoxycillin trihydrate and up to 30% sodium amoxycillin in combination with hydroxypropyl methylcellulose as a release retarding excipient.

Such formulations may comprise from 100 to 1250 mg amoxycillin which may be amoxycillin trihydrate or (crystallised) sodium amoxycillin or a mixture thereof, for instance 500, 875 or 1000 mg amoxycillin. Suitable excipients for slow release are those hereinbefore described for slow release layers. The formulation may comprise from 1 to 25%, preferably from 2 to 15%, more preferably 4 to 10% of xanthan gum, or from 10 to 25, preferably 15 to 20% of a hydroxypropyl-methylcellulose, for instance Methocel K100LV or Methocel K4M. Alternatively, such formulations may comprise citric acid, optionally with xanthan gum, as hereinbefore described.

Preferably, the unit dosage forms of the present invention are packaged in containers that inhibit the ingress of atmospheric moisture, for instance blister packs, tightly closed bottles or desiccated pouch packs etc which are conventional in the art. Preferably, bottles also include a desiccating material, to preserve the clavulanate. Preferred bottles include HDPE bottles. Preferred blister packs include cold-formed blister packs in which each blister may contain one tablet, or two tablets, where the unit dosage is two tablets, for instance 2×1000/62.5 mg tablets, to improve patient compliance.

The invention will now be described by way of example only with reference to the accompanying drawings, in which:

FIG. 1 shows the structure of various types of layered tablets of the present invention, in particular the structure of substantially cylindrical compressed tablets are shown in longitudinal section. In FIG. 1A, the tablet comprises a first layer (1) and a second layer (2), without any barrier layer or coating layer. In FIG. 1B, the tablet comprises a first layer (1), a second layer (2), and a barrier layer (3) sandwiched between the first and second layers (1) and (2). In FIG. 1C, the tablet comprises a first layer (1), a second layer (2), and a barrier layer (3) located on the end face of the second layer (2). In FIG. 1D, the tablet comprises a first layer (1), a second layer (2), a barrier layer (3) sandwiched between the first and second layers (1) and (2), and a coating layer (4) which partly covers the tablet. The dotted line shows the possibility of the coating layer (4A) covering the entire tablet. In FIG. 1E, the tablet comprises a first layer (1) a second layer (2), and a third layer (3) intermediate between the first and second layers (1) and (2). All three of these layers (1), (2) and (3) include active material content.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The foregoing examples describe tablet formulations which comprise potassium clavulanate. This is known to be extremely water sensitive. Therefore such tablet formulations should be made up in dry conditions, preferably at 30% relative humidity or less, and the ingredients of the formulation should be pre-dried where appropriate.

EXAMPLE 1
1000/62.5 mg Modified Release Tablet

| Ingredient | mg/tablet | % w/w |
|---|---|---|
| Immediate Release Layer | | |
| Amoxycillin Trihydrate (ERH <40%) | 654.1* | 40.88 |
| Potassium Clavulanate | 76.2# | 4.76 |
| Microcrystalline Cellulose | 136.4 | 8.52 |
| Sodium Starch Glycollate | 18.0 | 1.12 |
| Colloidal Silicon Dioxide | 6.3 | 0.39 |
| Magnesium Stearate | 9.0 | 0.56 |
| Total (Immediate Release Layer) | 900.0 | 56.23 |
| Slow Release Layer | | |
| Crystallised Sodium Amoxycillin | 480.8** | 30.05 |
| Microcrystalline Cellulose | 113.2 | 7.08 |
| Xanthan Gum | 14.0 | 0.87 |
| Citric Acid (anhydrous) | 78.0 | 4.87 |
| Colloidal Silicon Dioxide | 1.50 | 0.08 |
| Magnesium Stearate | 14.0 | 0.87 |
| Total (Sustained Release Layer) | 700.0 | 43.74 |
| Film coat | | |
| Opadry YS-1-7700-Composition: | | |
| Hydroxypropylmethylcellulose 2910 6 cp | 11.6 | |
| Hydroxypropylmethylcellulose 2910 15 cp | 3.9 | |
| Titanium dioxide | 15.1 | |
| Polyethylene Glycol 3350 | 2.3 | |
| Polyethylene Glycol 8000 | 2.3 | |
| Total weight of coated tablet | 1635.2 | |

*Equivalent to 562.5 mg of amoxycillin based on an assay of 86.0%
Equivalent to 62.5 mg of clavulanic acid based on an assay of 82.0%
**Equivalent to 437.5 mg amoxycillin based on an assay of 91.0%

EXAMPLE 2
1000/62.5 mg Modified Release Tablet
The immediate release layer and film coat are as for the tablet of Example 1

| Ingredient Slow Release Layer | mg/tablet | % w/w |
|---|---|---|
| Crystallised Sodium Amoxycillin | 480.8** | 30.05 |
| Microcrystalline Cellulose | 127.2 | 7.95 |
| Citric Acid (anhydrous) | 78.0 | 4.87 |
| Colloidal Silicon Dioxide | 1.5 | 0.09 |
| Magnesium Stearate | 14.0 | 0.87 |
| Total (Slow Release Layer) | 700.0 | 43.74 |
| Total Weight of coated tablet | 1635.2 | |

**Equivalent to 437.5 mg amoxycillin based on an assay of 91.0%

Figure 2A:
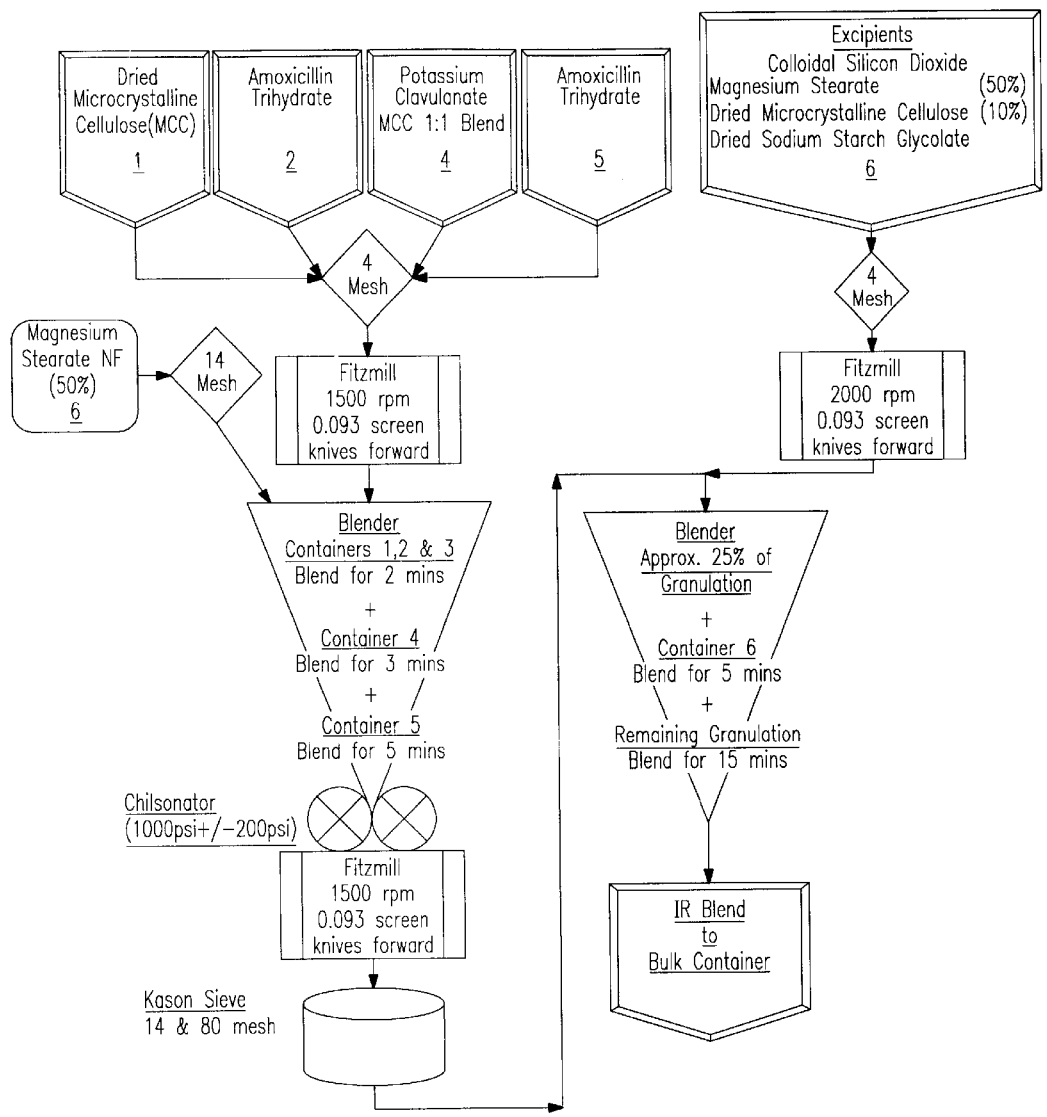
FIG. 2 demonstrates modified release tablets prepared according to the process flow diagram shown in FIG. 2. In brief, immediate and modified release blends are prepared which involve initial sieving and milling, as indicated, before roller compaction in a Chilsonater and further milling, sieving and blending.
Figure 2B:
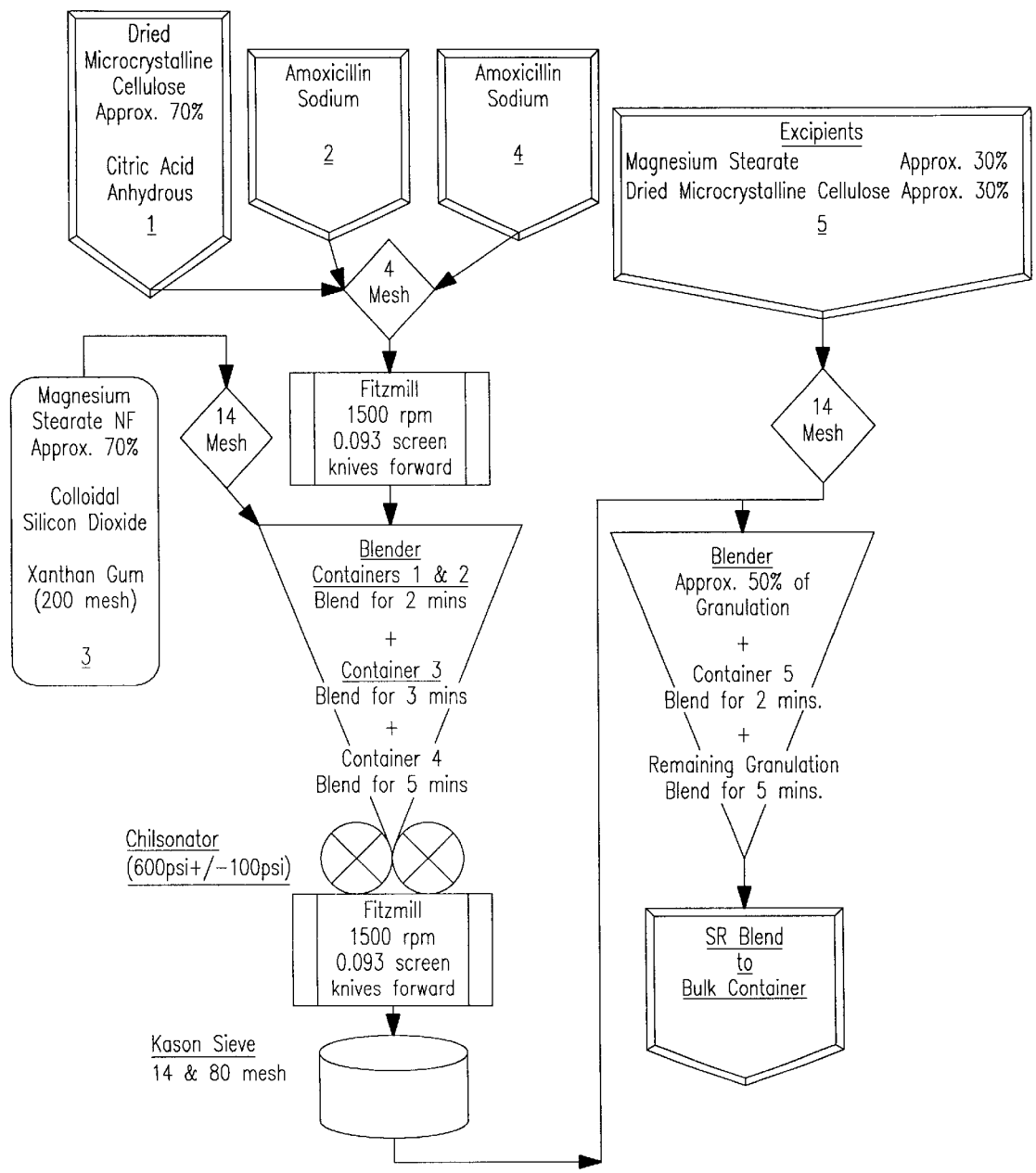
Figure 2C:
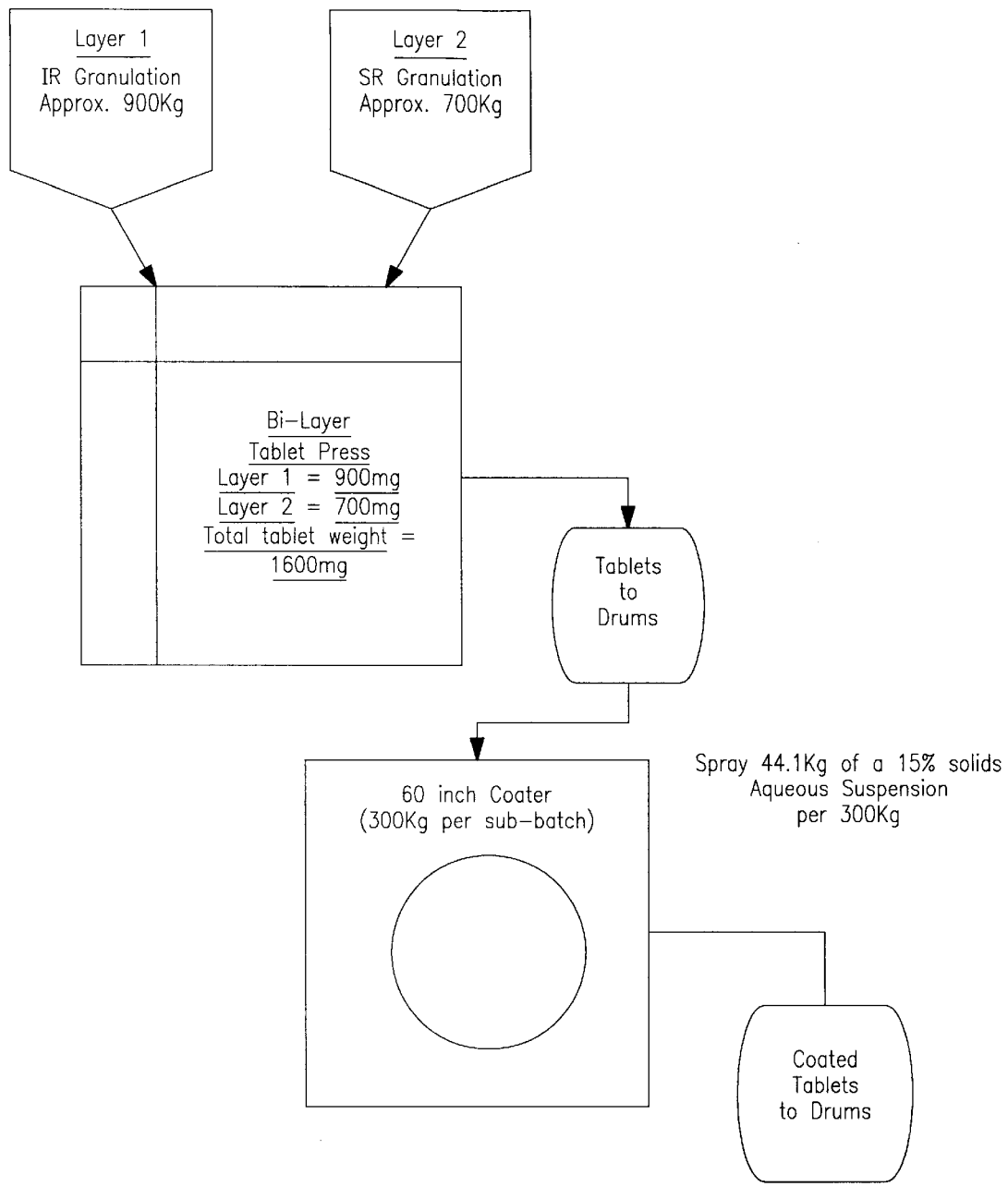

Preparation of Modified Release Tablets
Modified release tablets were prepared according to the process flow diagram shown in FIG. 2. In brief, immediate and modified release blends are prepared which involve initial sieving and milling, as indicated, before roller compaction in a Chilsonater and further milling, sieving and blending. The two containers comprising amoxycillin trihydrate and the two containers comprising sodium amoxycillin comprise about equal weights of amoxycillin trihydrate and sodium amoxycillin, respectively.

For the IR blend, the Chilsonator settings were: roll size, width=4 inches, diam=10 inches; hydraulic pressure= 900–1100 psi, air pressure=25–35 psi, roll speed=15–25 rpm, horizontal auger speed=15–30 rpm, vertical auger speed=300–350 rpm.

For the SR blend, the Chilsonator settings were: roll size, width=4 inches, diam=10 inches; hydraulic pressure= 500–700 psi, air pressure=15–20 psi, roll speed=15–25 rpm, horizontal auger speed=30–35 rpm, vertical auger speed= 300–350 rpm.

The two blends were then compressed as separate layers in a bilayer tablet press equipped with punches measuring 0.0406 inches by 0.8730 inches and having a modified capsule shape. For the first (immediate release) layer, there was no pre-compression, and a main compression of less than 10 KN. For the second layer, there was a pre-compression of less than 20 KN, and a main compression of less than 60 KN. The tablets thus produced had a total weight of 1600 mg±48 mg, a hardness in the range 8 to 18 SCU and a friability of less than 0.5%.

Finally, the tablet cores were coated with an aqueous film coating, using a 15% solids aqueous suspension, in a 60 inch coating pan which could accommodate up to 300 kg charge of tablets. The pan was equipped with 4 spray guns and rotated at 3 to 5 rpm. The inlet air was dehumidified with the temperature in the range 56 to 60° C. while the exhaust air humidity was in the range 4 to 12% and the temperature in the range 43 to 50° C. The spray rate was 80 to 120 ml/min/spray gun.

EXAMPLE 3
Slow Release Tablet (875 mg)

| | mg/tablet | % |
|---|---|---|
| (a) Sodium Amoxycillin Tablet | | |
| Crystallised Sodium Amoxycillin 91%* | 961.54 | 73.96 |
| Dried Microcrystalline Cellulose | 273.46 | 21.04 |
| Magnesium Stearate | 13.0 | 1.00 |
| Xanthan gum 200 mesh** | 52.0 | 4.00 |
| Total | 1300 | 100 |
| (b) Sodium Amoxycillin Tablet with citric acid | | |
| Crystallised Sodium Amoxycillin 91%* | 961.54 | 66.31 |
| Dried Microcrystalline Cellulose | 288.96 | 19.92 |
| Magnesium Stearate | 14.50 | 1.00 |
| Citric acid (anhydrous) | 156 | 10.75 |
| Xanthan gum 200 mesh** | 29.0 | 2.00 |
| Total | 1450 | 100 |
| (c) Amoxycillin Trihydrate Tablet | | |
| Amoxycillin Trihydrate 86%* | 1017.4 | 78.26 |
| Dried Microcrystalline Cellulose | 217.6 | 16.74 |

-continued

|  | mg/tablet | % |
|---|---|---|
| Magnesium Stearate | 13.0 | 1.00 |
| Xanthan Gum, 200 mesh** | 52.0 | 4.00 |
| Total | 1300 | 100 |

*adjusted for the potency of the amoxycillin component and corresponding to 875 mg amoxycillin.
**Xantural 75

EXAMPLE 4
875/62.5 mg Modified Release Tablet
Slow Release Layer

This may be formed using half the quantities given above, for a slow release layer comprising about 438 mg amoxycillin.

| Immediate release layer-1 | |
|---|---|
| Amoxycillin trihydrate | 507 mg |
| (equiv to amoxycillin free acid) | (438) |
| Potassium clavulanate | 71.8 |
| (equivalent to clavulanic acid) | (62.5) |
| Microcrystalline cellulose (Avicel PH102) | 125 |
| Sodium starch glycollate (Explotab) | 26 |
| Magnesium stearate | 6.5 |

The immediate release layer comprises nominally 438/62.5 mg amoxycillin/clavulanate.

| Immediate release layer-2 | |
|---|---|
| Amoxycillin trihydrate | 507 mg |
| (equiv to amoxycillin free acid) | (438) |
| Potassium clavulanate | 71.8 |
| (equivalent to clavulanic acid) | (62.5) |
| Microcrystalline cellulose (Avicel PH102) | 135 |
| Sodium starch glycollate (Explotab) | 34 |
| Talc | 67 |
| Magnesium stearate | 25 |
| Silica (Syloid) | 17 |

The immediate release layer comprises nominally 438/62.5 mg amoxycillin/clavulanate.

Barrier Layers

Barrier layers and methods for their preparation are described in WO 95/20946 (SmithKline Beecham) whose disclosure is incorporated herein by reference in its entirety.

Preparation of Tablets

The active ingredients, fillers and diluents (microcrystalline cellulose), release controlling agents (if present), disintegrants (crospovidone, sodium starch glycollate) etc are mixed. Lubricants (talc, Mg-stearate) and colloidal silicon dioxide (Syloid 244) are added, and mixing is continued for another minute. The complete mixture is slugged on a tablet press or roller compacted (briquetting step), followed by size reduction (Apex, Fitzmill, Frewitt) and passage through an oscillatory sieve or particle size classifier (Kason, Sweco). If the flow properties are unsatisfactory, the briquetting step is repeated. Separate compressed blends are prepared for the immediate and slow release layers, and barrier layer, if present.

In some cases, where the bulk density is rather low, a densifying step (pre-tabletting and sieving as in the briquetting method) may be required in order to achieve the nominal weight of a particular layer.

The blends are then compressed as separate layers on a layer tablet press to form bilayered tablets. Tablets may then be coated with a white opaque coating, for instance the product Opadry, Opaspray (Colorcon).

EXAMPLE 5
Dissolution Testing Methods

The release of amoxycillin and clavulanate from tablets into static media was measured using the <711> Dissolution Test, Apparatus 2, provided in USP 23, 1995.

| Test specifications: | |
|---|---|
| Temperature: | 37.0 ± 0.5° C. |
| Medium: | Deionized water, 900 mL |
| Paddle speed | 75 rpm |

Method

Aliquots of medium were removed for assay after 15, 30, 45, 60, 90, 120, 150, 180, 240, 300 360, 420 and 480 min, each aliquot being replaced simultaneously by an equal volume of medium to maintain constant volume. The amount of drug substance was determined by UV spectrometry, at 272 nM. The resulting dissolution profile for the tablets of Example 1 and 2 are shown as FIG. 3.

In vivo Pharmacokinetic Evaluation of Formulations

The bioavailability of dosages according to the present invention were evaluated in two human volunteer studies, Study A and Study B. These were open, randomised, crossover studies in healthy volunteers. Each dosage was administered with the aid of approximately 200 mL water, at the start of a light breakfast and after an overnight fast. Blood samples were collected into tubes containing EDTA at nominal times of pre-dose and 0.5, 1, 1.5, 2, 3, 4, 5, 6, 7, 8, 10 and 12 h after start of dosing, for assay of plasma levels of amoxycillin and clavulanate. Samples were cooled in an ice-bath awaiting further processing. Plasma was separated by refrigerated centrifugation at 4° C. and transferred to appropriately labelled polypropylene specimen containers and stored frozen at approximately −70° C. until assayed.

Samples were assayed for amoxycillin using a method based on protein precipitation with acetonitrile. Amoxycillin was extracted from human plasma (50 µL) by means of protein precipitation, using acetonitrile containing the internal standard and quantified by LC/MS/MS. Specifically, human plasma (50 µL) was pipetted into a 1.5 mL Eppendorf tube followed by the addition of acetonitrile containing the internal standard ([$^{13}C_6$]-amoxycillin, 200 µL). The tube was capped, vortex mixed and shaken for approximately 15 minutes. After centrifuging the sample (approximately 11,000×g, for 15 minutes), the supernatant was transferred to a silanised 1.1 mL tapered autosampler vial containing 200 µL of 5 mM ammonium acetate solution. An aliquot of extract was injected onto the HPLC/MS/MS system for analysis. The mass spectrometer was operated in positive ion mode, employing a Turbo IonSpray interface. Multiple reaction monitoring (MRM) was used to detect the components, amoxycillin and [$^{13}C_6$]-amoxycillin. The MRM procedure involves (1) mass selection of a characteristic ion of the required drug or internal standard in the first quadrupole mass analyser (2) fragmentation of the selected ion in the instrument's collision cell (3) detection of a fragment ion which is characteristic of the compound of interest. Quantification is performed by comparison of the chromatographic peak areas of the drug relative to the area of the internal standard. Linear responses in the analyte/ internal standard peak area ratios were observed for analyte concentrations ranging from 0.05 µg/mL (lower limit of quantification; LLQ) to 10 µg/mL (upper limit of quantitication: ULQ).

Samples were assayed for clavulanate using a method based on protein precipitation with acetonitrile. Clavulanate was extracted from human plasma by means of liquid/liquid using internal standard and quantified by LC/MS/MS. Specifically, human plasma (50 µL) was pipetted into a 1.5 mL Eppendorf tube followed by 0.2 mM ammonium acetate (200 µL) before addition of acetonitrile containing the internal standard (6-aminopenicillanic acid, 400 µL). The tube was capped, vortex mixed and shaken for approximately 20 minutes. After centrifuging the sample (approximately 14,500×g, for 15 minutes), the supernatant was transferred to a clean eppendorf tube and dichloromethane added. After further mixing and centrifugation (approximately 14, 500×g for 10 minutes) supernatent (no more than 150 uL) was transferred to a tapered 1.1 mL autosampler vial and left uncapped for at least 20 minutes to allow any traces of dichloromethane to evaporate. An aliquot of the extract was injected onto the HPLC/MS/MS system for analysis. The mass spectrometer was operated in positive ion mode, employing a Turbo IonSpray interface. Multiple reaction monitoring (MRM) was used to detect the components, clavulanate and 6-aminopenicillanic acid. The MRM procedure involves (1) mass selection of a characteristic ion of the required drug or internal standard in the first quadrupole mass analyser (2) fragmentation of the selected ion in the instrument's collision cell (3) detection of a fragment ion which is characteristic of the compound of interest. Quantification is performed by comparison of the chromatographic peak areas of the drug relative to the area of the internal standard. Linear responses in the analyte/ internal standard peak area ratios were observed for analyte concentrations ranging from 0.05 µg/mL (lower limit of quantification; LLQ) to 10 µg/mL (upper limit of quantitication: ULQ).

QC samples were assayed with each batch of samples against separately prepared calibration standards. The results of the QC samples were used to assess the day-to-day performance of the assay.

Plasma concentration-time data for each subject in each regimen were analysed by non-compartmental methods using the non-compartmental pharmacokinetic analysis program WinNonlin Professional Version 1.5. All calculations were based on actual sampling times. Pharmacokinetic parameters determined included maximum observed plasma concentration (Cmax) and time to reach maximum plasma concentration (Tmax). The apparent terminal elimination rate constant (lz) was derived from the log-linear disposition phase of the concentration-time curve using linear least-squares regression with visual inspection of the data to determine the appropriate number of points to calculate lz. The apparent terminal elimination half-life (T½) was calculated as ln(2)/lz.

Area under the plasma concentration-time curve from time zero to the last quantifiable plasma concentration [AUC(0-t)] was determined using the linear trapezoidal rule for each incremental trapezoid and the log trapezoidal rule for each decremental trapezoid [Chiou W. L., J. Pharmacokinet. Biopharm., 1978, 6, 539–547]. The area under the plasma concentration-time curve extrapolated to infinity [AUC(0-inf)] was calculated as the sum of AUC(0-t) and C(t)/lz, where C(t) was the predicted concentration from the log-linear regression analysis at the last measurable time point.

The time above the minimum inhibitory plasma concentration (T>MIC) was calculated manually by graphical interpolation, where the minimum inhibitory plasma concentrations was defined as 4 ug/mL for amoxycillin.

The mean concentration-time profiles for amoxycillin and for clavulanate were derived at each nominal sampling time for each formulation. In cases where a post-dose value was not quantifiable, a value of ½ the LLQ (0.050 ug/mL) was assigned to determine the mean value. Where the calculated mean value was less than the LLQ or was based on greater than 50% NQ values, a value of NQ was assigned for that sampling time.

$Log_e$-transformed Cmax and untransformed T>MIC for each of the formulations were analysed using Analysis of Covariance (ANCOVA) fitting a single term for formulation and fitting the data from the reference formulation as a co-variate. The 95% confidence intervals for the means of each formulation were constructed using the residual variance from the model. For Cmax, the confidence interval estimates on the log scale were then back-transformed to obtain the 95% confidence intervals of the geometric mean. These results were displayed graphically.

Assumptions underlying the analyses were assessed by inspection of residual plots. Homogeneity of variance was assessed by plotting the studentised residuals against the predicted values from the model, while normality was assessed using normal probability plots. Particular attention was paid to any outlying values observed with the reference formulation.

Study A

The first study compared three modified release dosages of 1750/125 mg (formulations I to III) and a fourth modified release dosages of 1500/125 mg (formulation IV) against an immediate release dosage of 1750/125 mg (formulation V), as follows:

(a) a dosage of 1750/125 mg amoxycillin/potassium clavulanate, made up of a combination of one modified release tablet comprising 875/125 mg amoxycillin trihydrate/clavulanate and 4% xanthan gum and one immediate release tablet comprising 875 mg amoxycillin trihydrate (formulation I);

(b) a dosage of 1750/125 mg amoxycillin/potassium clavulanate, made up of a combination of one modified release tablet comprising 875/125 mg crystallised sodium amoxycillin/clavulanate and 4% xanthan gum and one immediate release tablet comprising 875 mg amoxycillin trihydrate (formulation II);

(c) a dosage of 1750/125 mg amoxycillin/potassium clavulanate, made up of a combination of one modified release tablet comprising 875/125 mg crystallised sodium amoxycillin/clavulanate, citric acid (156 mg) and 2% xanthan gum and one immediate release tablet comprising 875 mg amoxycillin trihydrate (formulation III);

(d) a dosage of 1500/125 mg amoxycillin/potassium clavulanate (made up of a modified release tablet comprising 500/125 mg crystallised sodium amoxycillin/potassium clavulanate and two immediate release tablet comprising 500 mg amoxycillin trihydrate (Amoxyl, SmithKline Beecham) (formulation IV); and (e) a dosage of 1750/125 mg amoxycillin/potassium clavulanate, made up of a combination of one immediate release tablet comprising 875/125 mg amoxycillin trihydrate/clavulanate (Augmentin, SmithKline Beecham) and one immediate release tablet comprising 875 mg amoxycillin trihydrate (Amoxyl, SmithKline Beecham) (formulation V).

| Results | | | | |
|---|---|---|---|---|
| Formulation | n | Cmax[1] | T > MIC[1,2] | AUC[1,3] |
| I | 8 | 12.75 (4.96) | 4.5 (1.8) | 47.83 |
| II | 8 | 18.56 (4.72) | 4.4 (1.0) | 57.46 |
| III | 8 | 13.03 (2.34) | 5.73 (2.54) | 54.93 |
| IV | 8 | 17.33 (4.66) | 4.8 (0.9) | 56.71 |
| V | 40 | 20.21 (6.09) | 4.2 (0.9) | 56.33 |

()standard deviation
[1]arithmetic mean value
[2]T > MIC is the time (h) above an amoxycillin concentration of 4 μg/ml
[3]Area under the curve (0 to 12 h, μg.h/mL)

Figure 4:
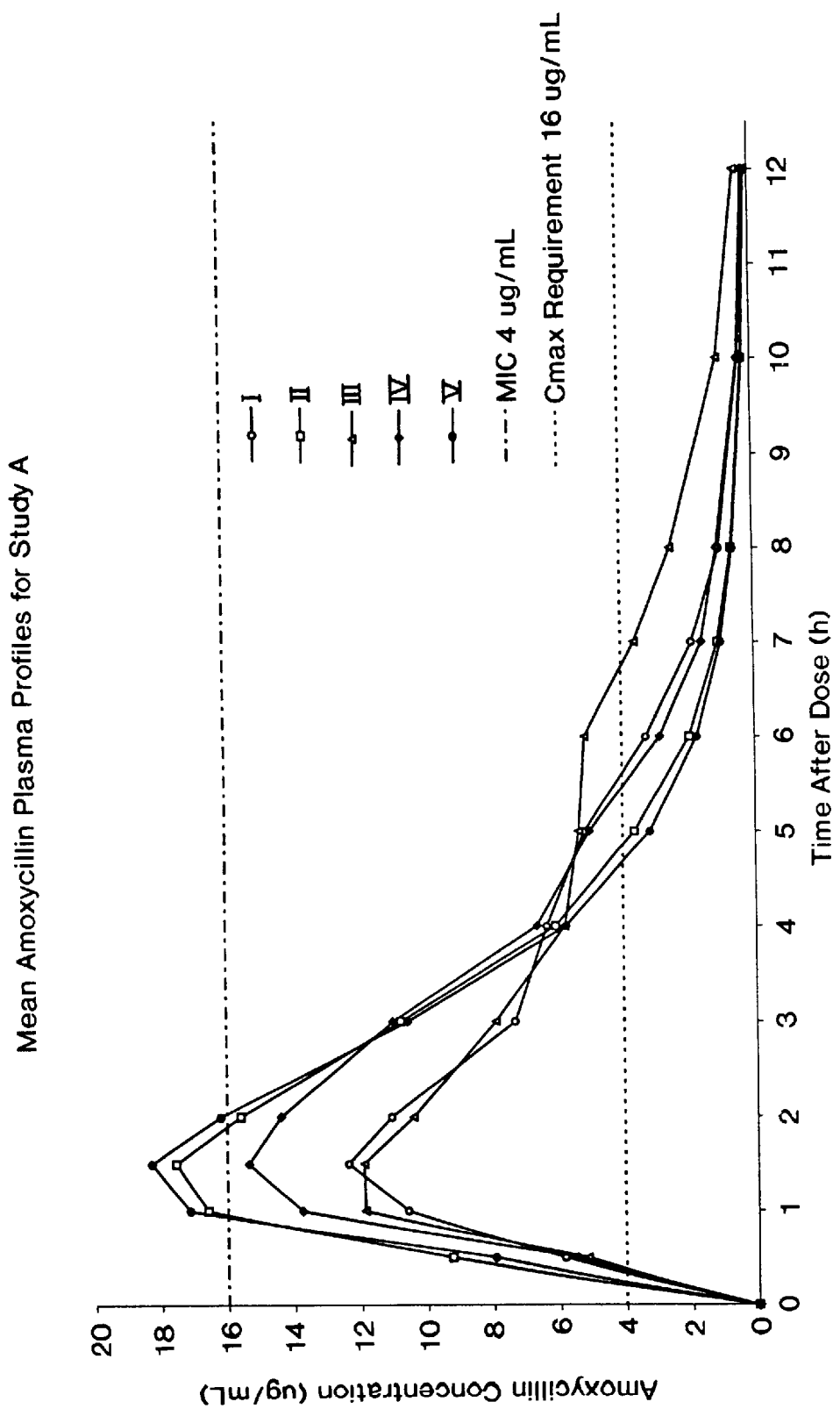
FIG. 4 demonstrate the pharmacokinetic profiles of Study A

The pharmacokinetic profile is shown in FIG. 4.

Study B

The second study investigated two different modified release dosages of 2000/125 mg (formulations VI and VII) against an immediate release dosage of 2000/125 mg (formulation VIII), as follows:

(a) a dosage of 2000/125 mg amoxycillin/potassium clavulanate, made up of two bilayer tablets according to Example 1 (formulation VI);

(b) a dosage of 2000/125 mg amoxycillin/potassium clavulanate, made up of two bilayer tablets according to Example 2 (formulation VII);

(c) a dosage of 2000/125 mg amoxycillin/potassium clavulanate, made up of a combination of three tablets each comprising 500 mg amoxycillin (Amoxyl, SmithKline Beecham) and one tablet comprising 500 mg amoxycillin and 125 mg potassium clavulanate (Augmentin, SmithKline Beecham) (formulation VIII).

| Results | | | | | |
|---|---|---|---|---|---|
| Formulation | N | Cmax[1] | T > MIC[1,2] | T > MIC[1,3] | AUC[1,4] |
| VI | 7 | 17.41 (1.93) | 6.0 (1.3) | 4.8 (1.2) | 74.9 |
| VII | 8 | 17.46 (6.02) | 5.9 (1.3) | 4.0 (1.3) | 71.5 |
| VIII | 12 | 23.75 (5.73) | 4.9 (1.1) | 3.5 (1.0) | 69.2 |

()standard deviation
[1]arithmetic mean value
[2]T > MIC is the time (h) above an amoxycillin concentration of 4 μg/ml
[3]T > MIC is the time (h) above an amoxycillin concentration of 8 μg/ml
[4]Area under the curve (0 to 12 h, μg.h/mL).

Comparison of the AUC values for formulations VI and VII (bilayer tablets) against VIII (immediate release tablets) shows that the absorption of the amoxycillin component has not been compromised by formulating a part of it in a slow release layer. This means that there is no extra, unabsorbed amoxycillin which may otherwise cause problems further down in the GI tract, for instance due to a lack of absorption and destruction of symbiotic bacteria It was also found that for formulation VI, there was less inter-subject variability in the amoxycillin plasma concentrations than for formulation VII. These formulations were the same, except that formulation VI also comprised xanthan gum (2%) in the slow release layer.

The pharmacokinetic profile for amoxycillin plasma concentration is shown in FIG. 5 (in which A is formulation VI, B is formulation VII, D is formulation VIII).

The pharmacokinetic profile for the clavulanate component was substantially the same for the bilayer tablets and the immediate release tablets, showing that the bioavailability thereof was not compromised by incorporation into the immediate release layer of a bilayer tablet.

The present invention also extends to formulations which are bioequivalent to the tablets of formulations VI and VII, in terms of both rate and extent of absorption, for instance as defined by the US Food and Drug Administration and discussed in the so-called "Orange Book" (Approved Drug Products with Therapeutic Equivalence Evaluations, US Dept of Health and Human Services, 19th edn, 1999).

Reference Data

The existing Augmentin 875/125 mg tablet has a $C_{max}$ value of 11.6±2.8 μg/ml (Physicians Desk Reference, Medical Economics Co, 52 edition, 1998, 2802). The time above MIC was about 40% of the 12 hour dosing interval for an MIC of 2 μg/ml and about 30% for an MIC of 4 μg/ml (SmithKline Beecham data).

What is claimed is:

1. A modified release pharmaceutical composition comprising compacted granules of a pharmaceutically acceptable soluble salt of amoxycillin and at least one pharmaceutically acceptable organic acid which are admixed, as solids, in intimate contact at a ratio from about 20:1 to 1:2 (of the pharmaceutically acceptable soluble salt of amoxycillin to the at least one pharmaceutically acceptable organic acid), and a pharmaceutically acceptable diluent or compression aid.

2. A modified release composition according to claim 1 in the form of a tablet.

3. A modified release composition according to claim 1 wherein the pharmaceutically acceptable soluble salt of amoxycillin is comprises crystallized sodium amoxycillin.

4. A composition according to claim 1 wherein the pharmaceutically acceptable soluble salt of amoxycillin is sodium amoxycillin.

5. A composition according to claim 1 wherein the at least one pharmaceutically acceptable organic acid is selected from pharmaceutically acceptable monocarboxylic and polycarboxylic acids having from 2 to 25 carbon atoms, pharmaceutically acceptable monocyclic aryl and polycyclic aryl acids, and pharmaceutically acceptable monohydrogen and dihydrogen metal salts of any of the foregoing multivalent acids.

6. A composition according to claim 1 wherein the at least one pharmaceutically acceptable organic acid is selected from pharmaceutically acceptable monocarboxylic and polycarboxylic acids having from 2 to 10 carbon atoms and an acidic salt of any of the foregoing.

7. A composition according to claim 1 wherein the at least one pharmaceutically acceptable organic acid is selected from $C_{(2-10)}$ alkyl- and $C_{(2-10)}$ alkenyl-carboxylic acids having one, two, or three carboxylic acid groups, and optionally at least one hydroxy substituent, and optionally at least one —CO group in the carbon chain and an acidic salt of any of the foregoing.

8. A composition according to claim 1 wherein the at least one pharmaceutically acceptable organic acid is selected from malonic acid, succinic acid, fumaric acid, maleic acid, adipic acid, lactic acid, levulinic acid, sorbic acid, tartaric acid, malic acid, ascorbic acid, citric acid, and an acidic salt of any of the foregoing.

9. A composition according to claim 1 wherein the at least one pharmaceutically acceptable organic acid is citric acid.

10. A composition according to claim 1 wherein the at least one pharmaceutically acceptable organic acid is citric acid anhydrous.

11. A composition according to claim 1 wherein the amount of the pharmaceutically acceptable soluble salt of amoxycillin is about 438 mg +/−5%.

12. A composition according to claim 1 wherein the granules further comprise at least one release retarding excipient which is selected from pH sensitive polymers, release-retarding polymers which exhibit swelling characteristics when in an aqueous environment, polymeric materials which exhibit gelling characteristics when in an aqueous environment, and polymeric materials which exhibit both swelling and gelling characteristics when in an aqueous environment.

13. A composition according to claim 12 wherein the at least one release retarding excipient is selected from methylcellulose, carboxymethylcelluloses, low-molecular weight hydroxypropylmethylcellulose, low-molecular weight polyvinylalcohol, polyoxyethyleneglycol, and noncross-linked polyvinylpyrrolidone.

14. A composition according to claim 12 wherein the at least one release retarding polymer is selected from medium-viscosity hydroxypropylmethylcellulose, and medium viscosity polyvinylalcohol.

15. A composition according to claim 12 wherein the at least one release retarding excipient is xanthan gum.

16. A composition according to claim 15 wherein the xanthan gum is present in an amount from about 0.5% to about 8% by weight.

17. A composition according to claim 15 wherein the xanthan gum is present in an amount from about 1% to about 5% by weight.

18. A composition according to claim 15 wherein the xanthan gum is pharmaceutical grade xanthan gum, 200 mesh.

19. A composition according to claim 1 wherein the diluent is lactose.

20. A composition according to claim 1 wherein the compression aid is microcrystalline cellulose.

21. A composition according to claim 1 wherein the pharmaceutically acceptable soluble salt of amoxycillin and the at least one pharmaceutically acceptable organic acid are admixed in intimate contact such that upon exposure to an aqueous environment they interact such that the rate of release of amoxycillin from the solid form of the second release phase is reduced when compared to the rate of release of amoxycillin from an immediate release formulation.

* * * * *